US012215362B2

(12) United States Patent
Kwak et al.

(10) Patent No.: US 12,215,362 B2
(45) Date of Patent: *Feb. 4, 2025

(54) PHARMACEUTICAL COMPOSITION FOR PREVENTION OR TREATMENT OF HEART FAILURE

(71) Applicant: BETHPHAGEN INC., Gwangju (KR)

(72) Inventors: Tae Hwan Kwak, Yongin-si (KR); Woo Jin Park, Gwangju (KR)

(73) Assignee: BETHPHAGEN INC., Gwangju (KR)

( * ) Notice: Subject to any disclaimer, the term of this patent is extended or adjusted under 35 U.S.C. 154(b) by 1350 days.

This patent is subject to a terminal disclaimer.

(21) Appl. No.: 16/651,779

(22) PCT Filed: Sep. 28, 2018

(86) PCT No.: PCT/KR2018/011521
§ 371 (c)(1),
(2) Date: Mar. 27, 2020

(87) PCT Pub. No.: WO2019/066548
PCT Pub. Date: Apr. 4, 2019

(65) Prior Publication Data
US 2020/0239862 A1 Jul. 30, 2020

(30) Foreign Application Priority Data
Sep. 29, 2017 (KR) .......... 10-2017-0127442

(51) Int. Cl.
*A61P 9/00* (2006.01)
*A61K 35/76* (2015.01)
*A61K 38/17* (2006.01)
*A61K 48/00* (2006.01)
*C07K 14/47* (2006.01)
*C12N 7/00* (2006.01)
*C12N 9/14* (2006.01)
*C12N 15/85* (2006.01)
*C12N 15/86* (2006.01)
*G01N 33/68* (2006.01)
*A61K 38/00* (2006.01)

(52) U.S. Cl.
CPC .......... *C12N 9/14* (2013.01); *A61K 35/76* (2013.01); *A61K 38/1738* (2013.01); *A61K 38/179* (2013.01); *A61K 48/0066* (2013.01); *A61P 9/00* (2018.01); *C07K 14/47* (2013.01); *C12N 7/00* (2013.01); *C12N 15/85* (2013.01); *C12N 15/86* (2013.01); *C12Y 306/03008* (2013.01); *G01N 33/6893* (2013.01); *A61K 38/00* (2013.01); *A61K 48/00* (2013.01); *C12N 2750/14143* (2013.01); *C12N 2800/107* (2013.01); *G01N 2800/325* (2013.01)

(58) Field of Classification Search
None
See application file for complete search history.

(56) References Cited

U.S. PATENT DOCUMENTS

| 7,101,850 B2 * | 9/2006 | Levine | C07K 16/22 |
| | | | 514/13.3 |
| 11,761,019 B2 * | 9/2023 | Lee | C12N 15/86 |
| | | | 435/69.1 |
| 2009/0239940 A1 | 9/2009 | Del Monte et al. | |
| 2013/0287739 A1 | 10/2013 | Hajjar et al. | |
| 2013/0345130 A1 | 12/2013 | Park et al. | |
| 2017/0014494 A1 * | 1/2017 | Hajjar | A61K 38/50 |
| 2018/0369324 A1 * | 12/2018 | Park | A61K 38/17 |

FOREIGN PATENT DOCUMENTS

| CN | 103648506 A | 3/2014 |
| KR | 10-2011-0105957 A | 9/2011 |
| KR | 10-2017-0056460 A | 5/2017 |

(Continued)

OTHER PUBLICATIONS

Verboomen, H., Wuytack, F., Van den Bosch, L., Mertens, L. and Casteels, R., 1994. The functional importance of the extreme C-terminal tail in the gene 2 organellar Ca2+-transport ATPase (SERCA2a/b). Biochemical Journal, 303(3), pp. 979-984. (Year: 1994).*

Anthony S. Fargnoli et al., "Gene Therapy in Heart Failure", Handbook of Experimental Pharmacology, 2016 (27 pages total).

Raad et al., "Safety and efficacy of a combinatorial CCN5/SERCA2A gene delivery approach for arrhythmia suppression in a chronic model of angiotensin II (ANG) induced cardiac hypertrophy and failure", Database Embase, Emb-628264505, Circulation Research, vol. 123, No. 1, American Heart Association's Basic Cardiovascular Sciences 2018 Scientific Sessions: Innovating in Cardiovascular Research, BCVS 2018, 2018, Jul. 29-Aug. 2 at San Antonio, TX, Abstract, 2 pages.

(Continued)

*Primary Examiner* — Neil P Hammell
*Assistant Examiner* — Khaleda B Hasan
(74) *Attorney, Agent, or Firm* — Sughrue Mion, PLLC

(57) ABSTRACT

The present invention relates to a pharmaceutical composition for prevention and treatment of heart failure. Specifically, the present invention relates to a gene construct comprising a polynucleotide coding for SERCA2a protein or a fragment thereof and a polynucleotide coding for CCN5 protein or a fragment thereof, and a pharmaceutical composition comprising the same construct as an effective ingredient for preventing or treating heart failure. A pharmaceutical composition for prevention and treatment of heart failure according to the present invention is used in a method for co-expression of SERCA2a protein and CCN5 protein. Designed to exert a synergistic therapeutic effect through SERCA2a protein's function of preventing the loss of cardiomyocytes and increasing the activity of cardiomyocytes and CCN5 protein's function of suppressing the fibrosis of heart cells and tissues, the pharmaceutical composition can be useful for preventing or treating heart failure, which is a complex disorder induced by various etiological factors.

27 Claims, 32 Drawing Sheets
Specification includes a Sequence Listing.

(56) References Cited

FOREIGN PATENT DOCUMENTS

| WO | 2007054250 A1 | 5/2007 |
|---|---|---|
| WO | 2011/118928 A2 | 9/2011 |
| WO | 2013/010135 A1 | 1/2013 |
| WO | 2016/055437 A1 | 4/2016 |
| WO | 2017/083750 A1 | 5/2017 |

OTHER PUBLICATIONS

Kim et al., "High Cleavage Efficiency of a 2A Peptide Derived from Porcine Teschovirus-1 in Human Cell Lines, Zebrafish and Mice", PLoS One, e18556, vol. 6, Issue 4, Apr. 2011, pp. 1-8.
Jeong et al., "Matricellular Protein CCN5 Reverses Established Cardiac Fibrosis", Journal of the American College of Cardiology, 2016, vol. 67, No. 13, pp. 1556-1568 (13 pages total).
Greenberg, "Gene therapy for heart failure", Journal of Cardiology, 2015, vol. 66, pp. 195-200 (6 pages total).
GenBank: AIC55480.1, WISP2, partial [synthetic construct] Mar. 19, 2015.
GenBank: AF100780.2, *Homo sapiens* connective tissue growth factor related protein WISP-2 (WISP2) mRNA, complete cds, Dec. 14, 2016.
GenBank: KU665997.1, Cloning vector pPV512, complete sequence, May 4, 2016.
Eugene Braunwald, "The war against heart failure: the Lancet lecture", The Lancet, Nov. 16, 2014, 13 pages, vol. 385.
Barry J. Maron et al., "Contemporary Definitions and Classification of the Cardiomyopathies : An American Heart Association Scientific Statement From the Council on Clinical Cardiology, Heart Failure and Transplantation Committee; Quality of Care and Outcomes Research and Functional Genomics and Translational Biology Interdisciplinary Working Groups; and Council on Epidemiology and Prevention", Circulation, Mar. 27, 2006, pp. 1807-1816, vol. 113.
Al-Hsien Li et al., "Dynamic Changes in Myocardial Matrix and Relevance to Disease: Translational Perspectives", Circulation Research, Feb. 28, 2014, pp. 916-927, vol. 114, No. 5.
Norimichi Koitabashi et al., "Reverse remodeling in heart failure mechanisms and therapeutic opportunities", Nature Reviews Cardiology, Mar. 2012, pp. 147-157 vol. 9.
Jana S. Burchfield, PhD., et al., "Pathological Ventricular Remodeling Mechanisms: Part 1 of 2", Circulation, pp. 388-400, Jul. 23, 2013, vol. 128.
Thomas G. Von Lueder et al., "New medical therapies for heart failure", Nature Reviews Cardiology, 2015, pp. 730-740, vol. 12.
Przemek A. Gorski et al., "Altered Myocardial Calcium Cycling and Energetics in Heart Failure—A Rational Approach for Disease Treatment", Cell Metabolism, Feb. 3, 2015, pp. 183-194, vol. 21.
Melvin Y. Rincon et al., "Gene Therapy for Cardiovascular Disease: Advances in Vector Development, Targeting and Delivery for Clinical Translation", Cardiovascular Research, Aug. 3, 2015, pp. 4-20, vol. 108.
Muthiah Vaduganathan et al., "The disconnect between phase II and phase III trials of drugs for heart failure", Nature Reviews Cardiology, Feb. 2013, pp. 85-97, vol. 10.
International Search Report for PCT/KR2018/011521 dated Apr. 17, 2019 [PCT/ISA/210].

\* cited by examiner

[Fig. 1a]
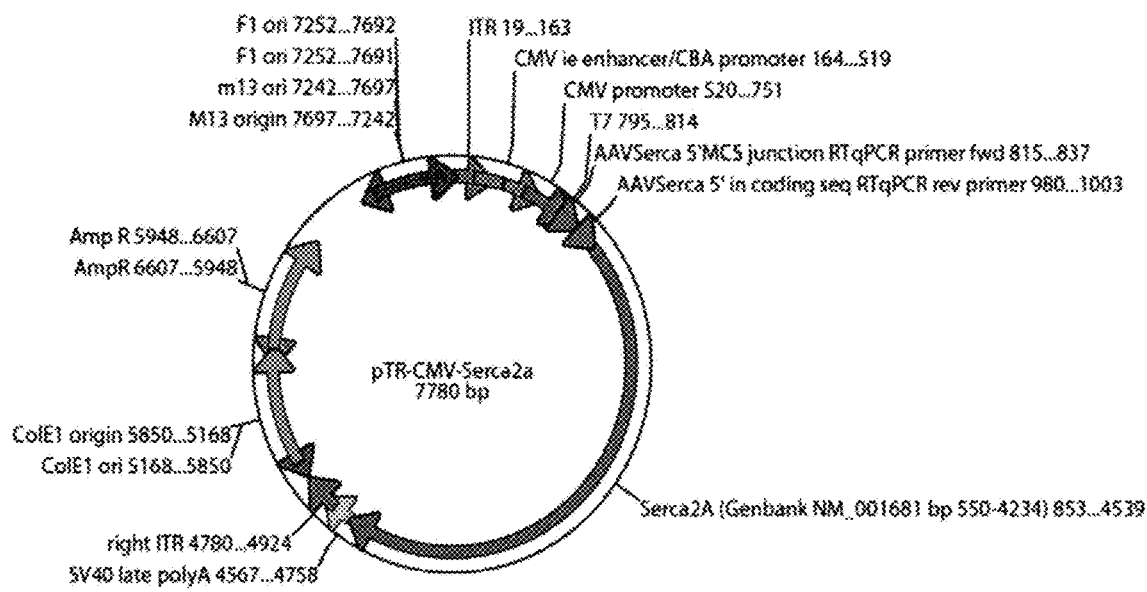

[Fig. 1b]
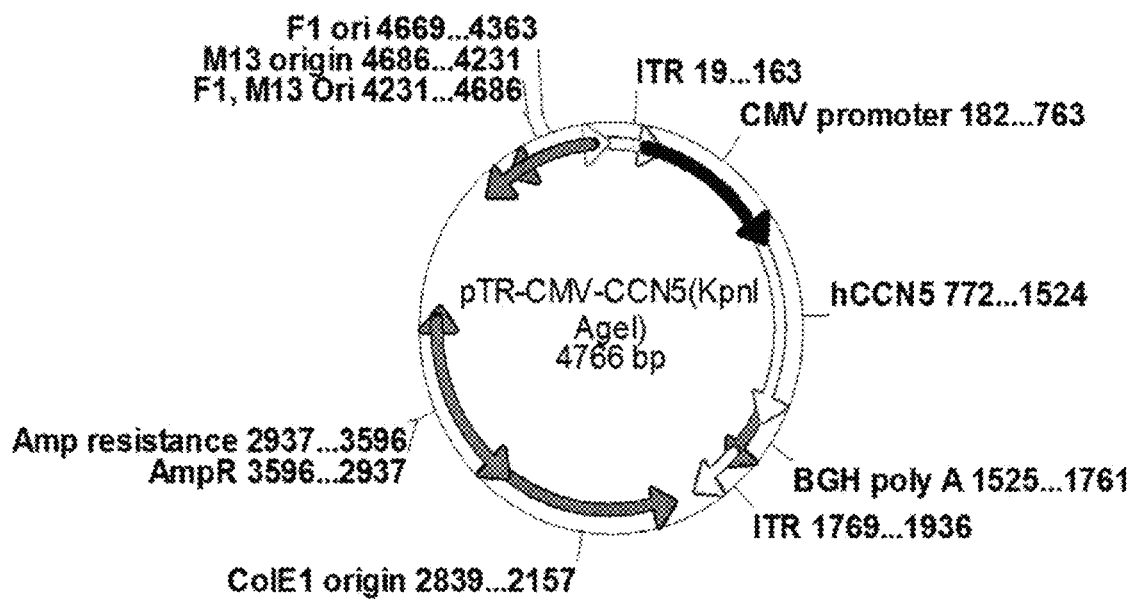

[Fig. 1c]
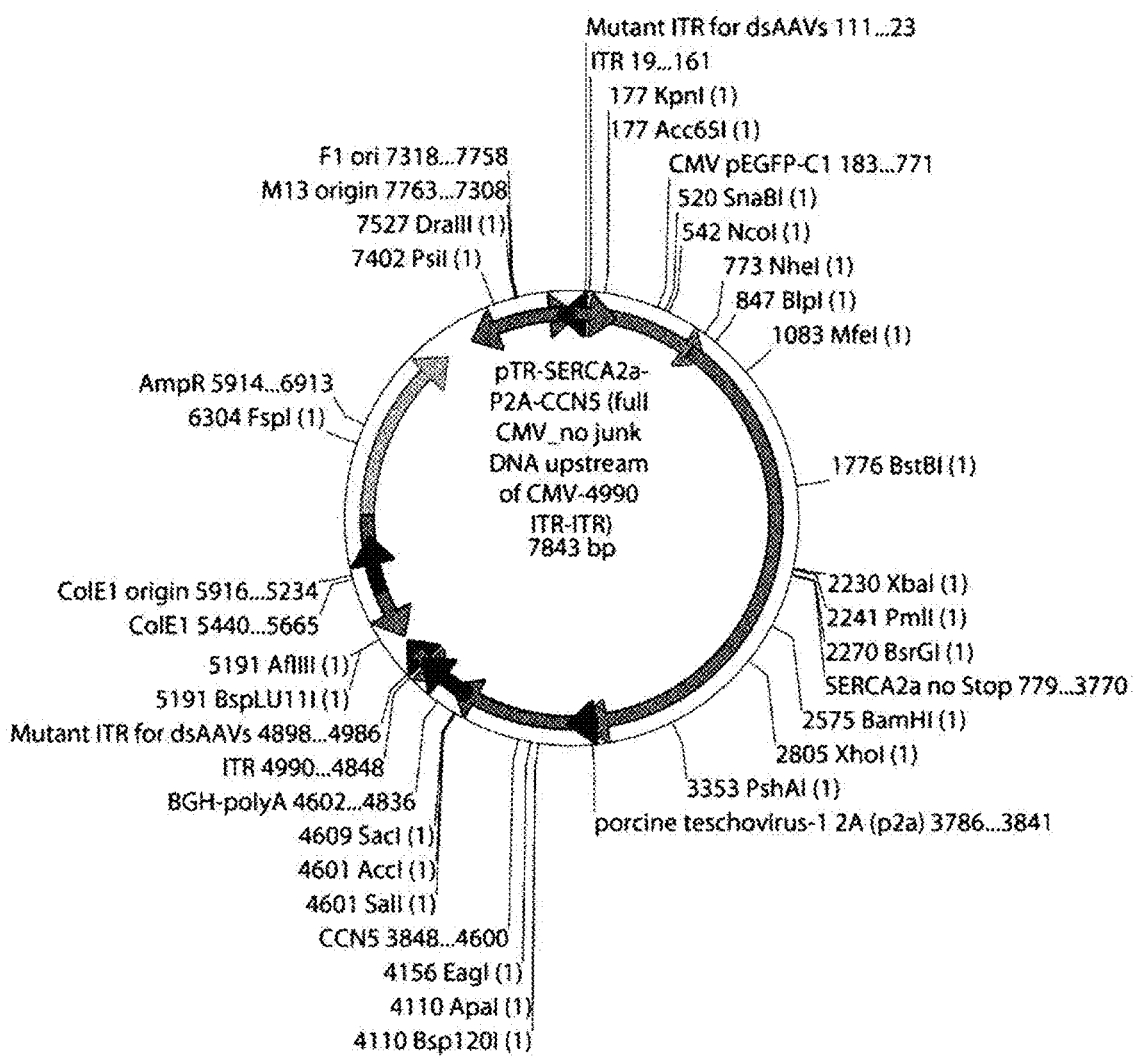

[Fig. 1d]
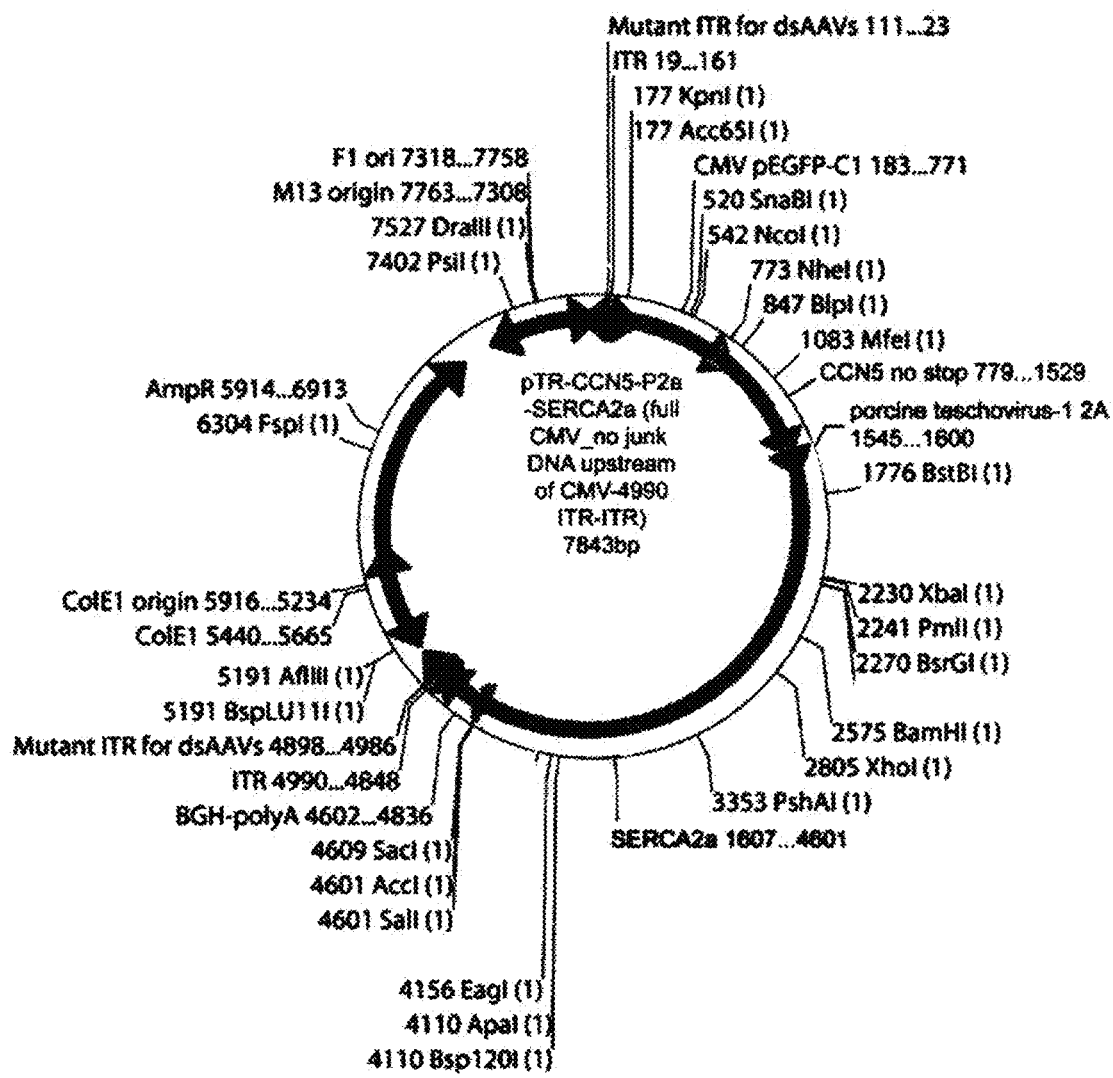

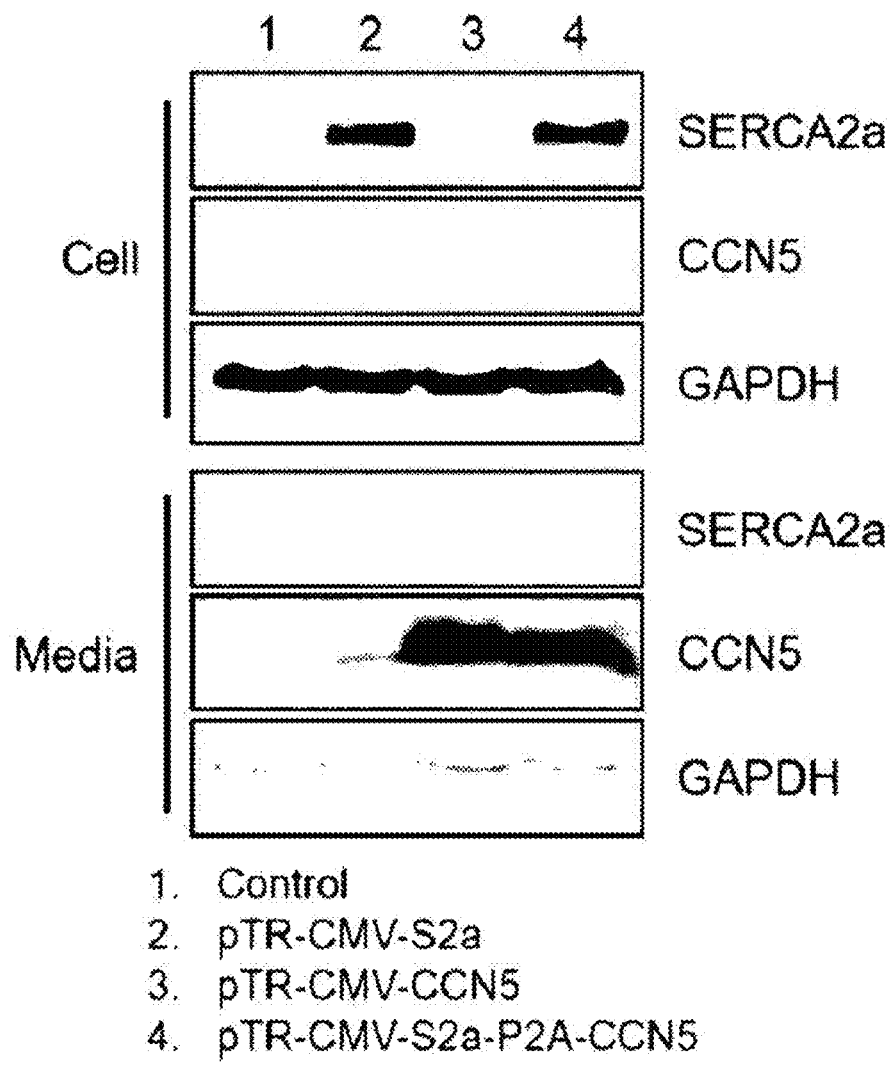
[Fig. 2a]

[Fig. 2b]
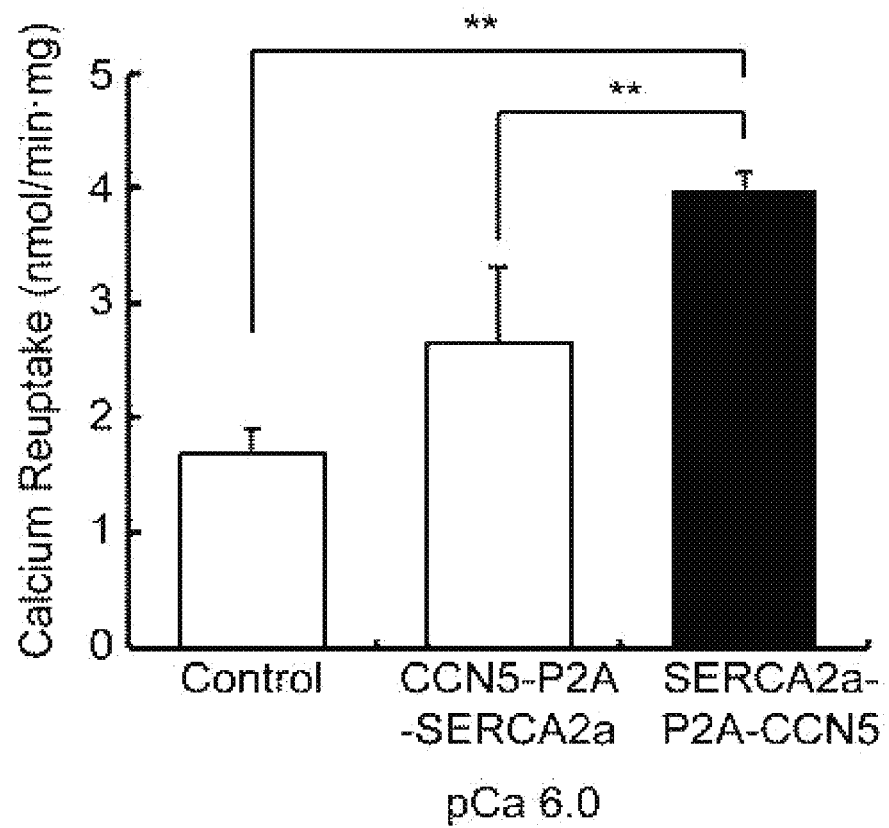

[Fig. 2c]
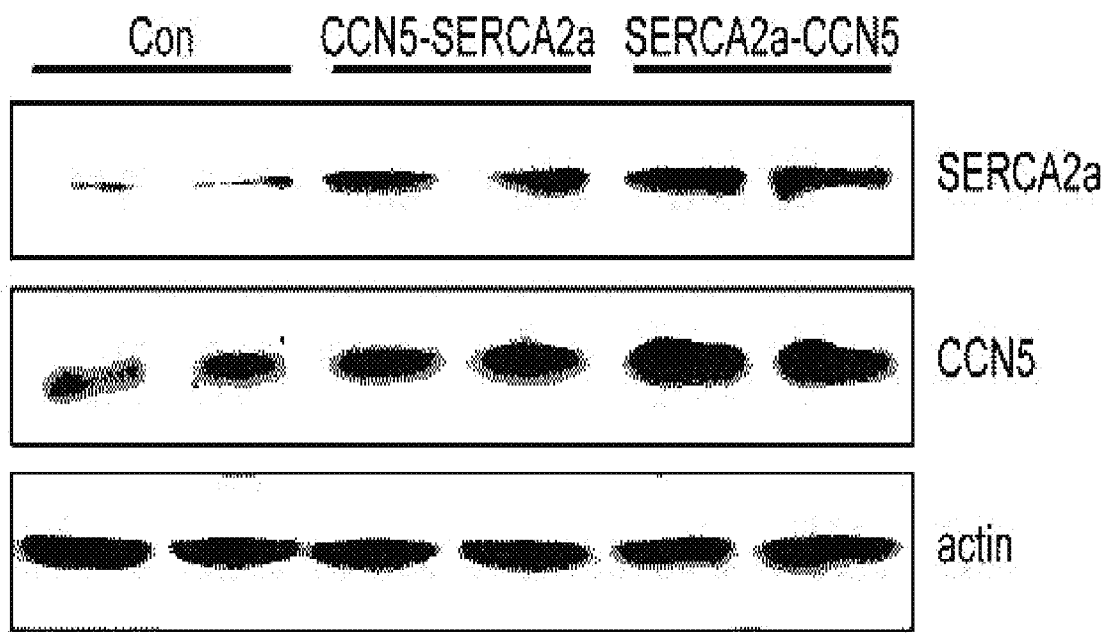

[Fig. 3]
Groups
- Sham
- I/R 30 min + AAV9-control (1E11vg, n=5)
- I/R 30 min + AAV9-SERCA2a (1E11vg, n=5)
- I/R 30 min + AAV9-CCN5 (1E11vg, n=5)
- I/R 30 min + AAV9-SERCA2a / AAV9-CCN5 (1E11vg each, , n=5)
Method
- LAD ligation for 30 minutes and reperfusion for one month
- Injection method : tail vein injection during LAD ligation

[Fig. 4a]
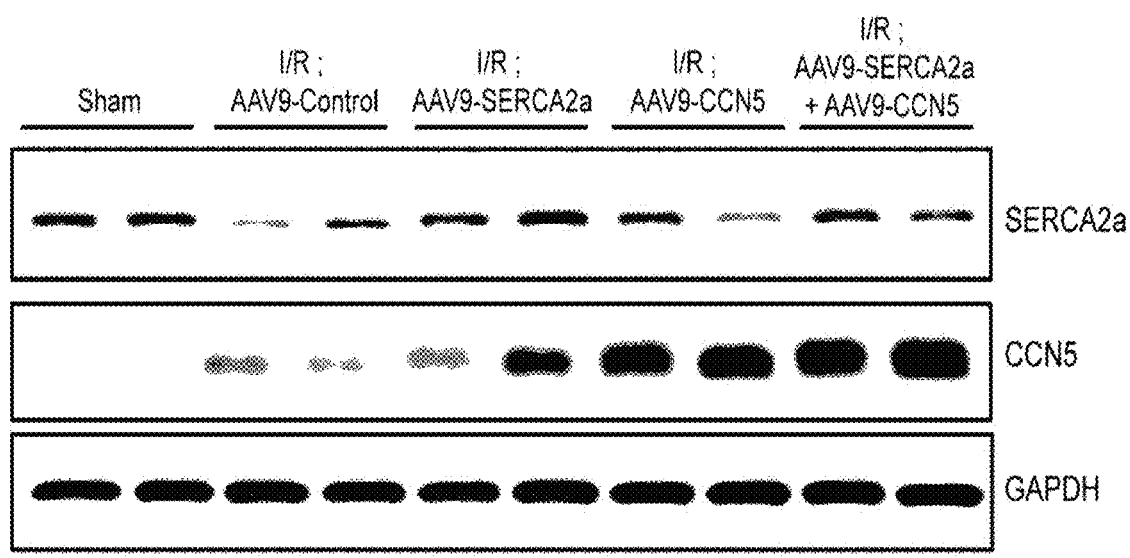

[Fig. 4b]
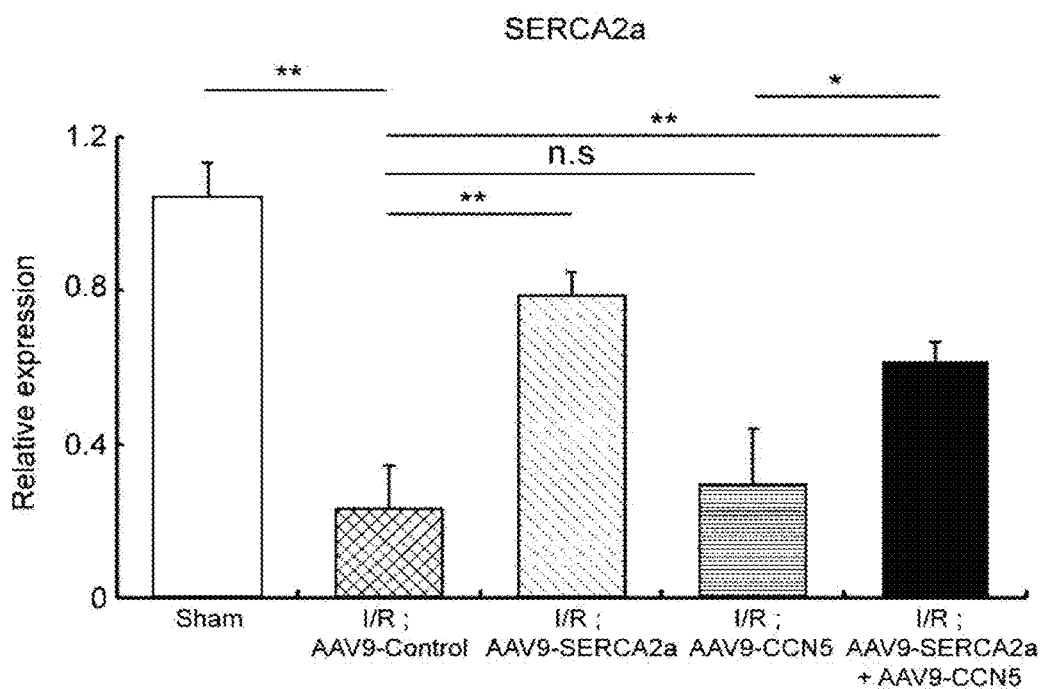

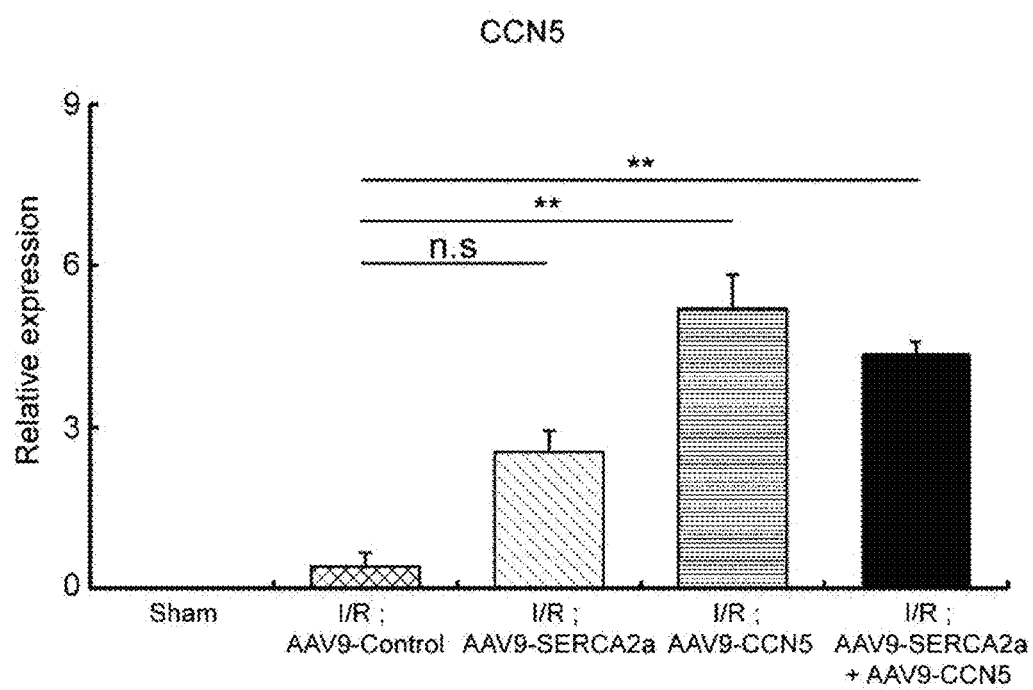
[Fig. 4c]

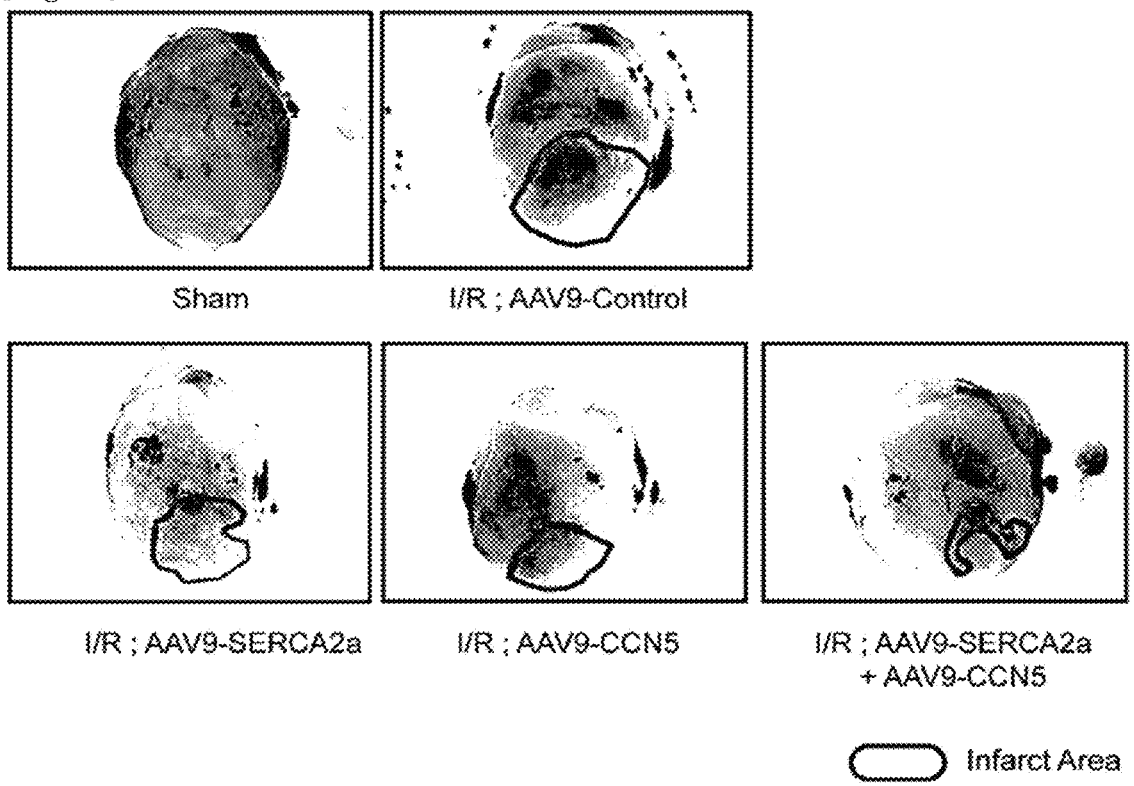

[Fig. 6]
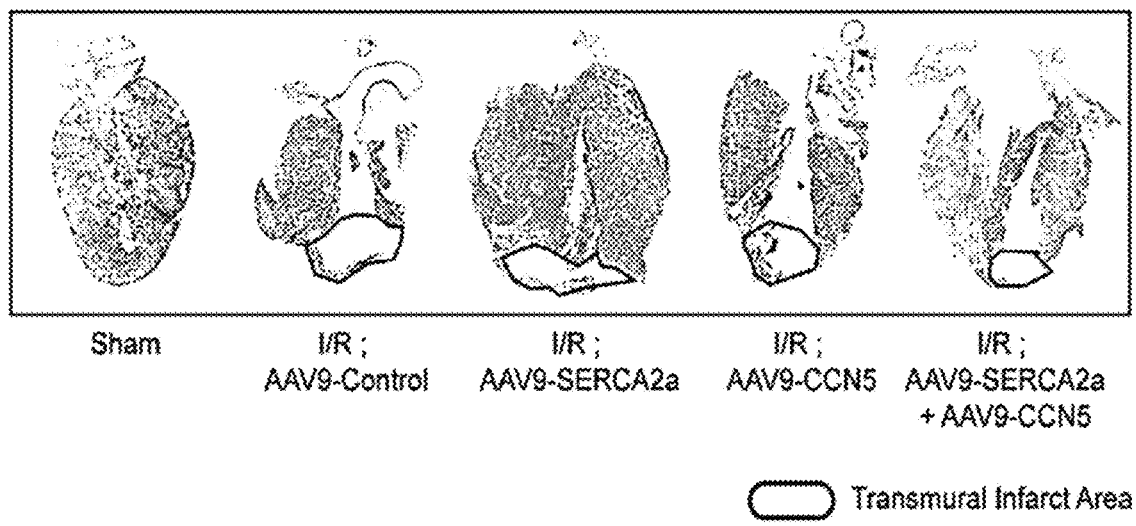

[Fig. 7]
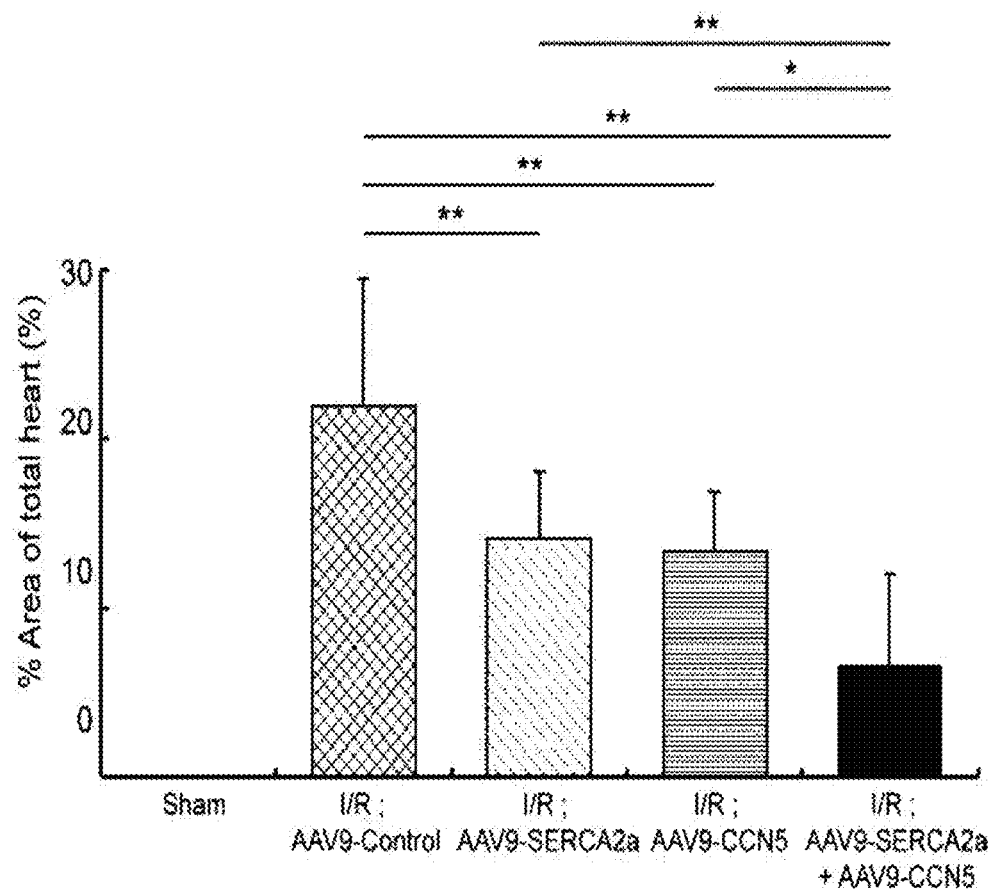

[Fig. 8]
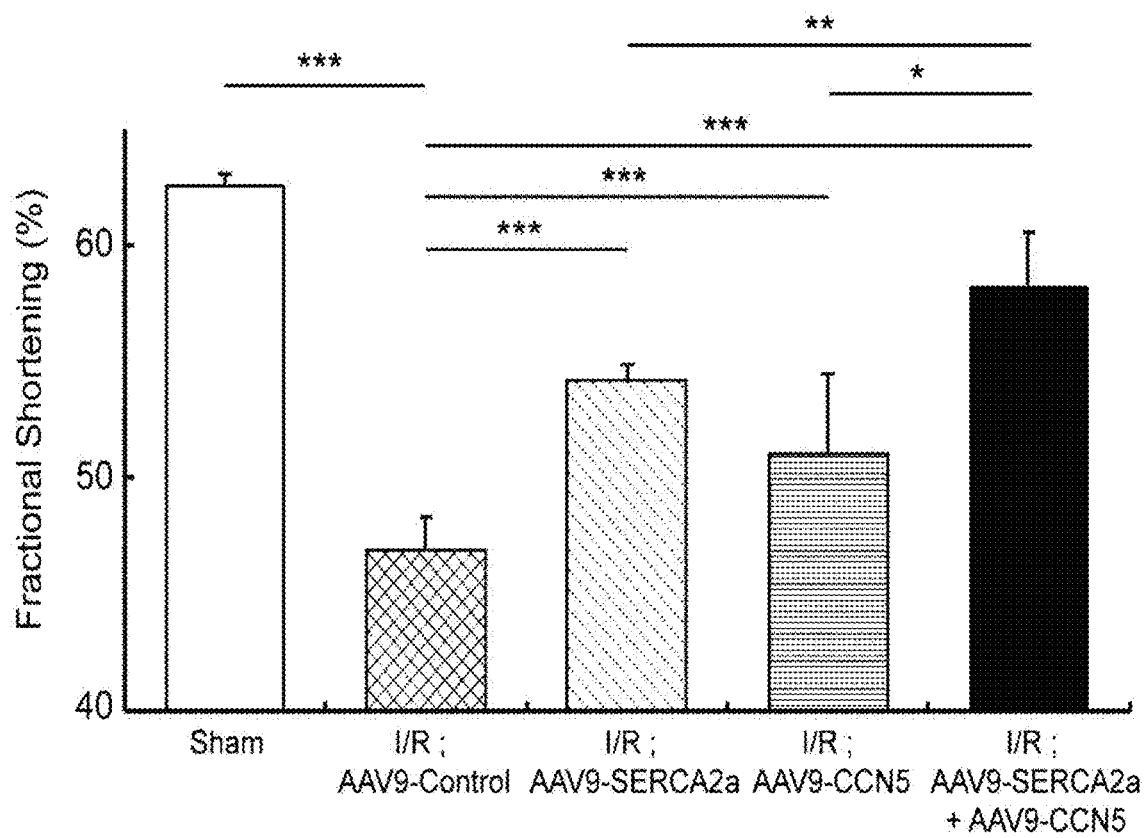

[Fig. 9a]
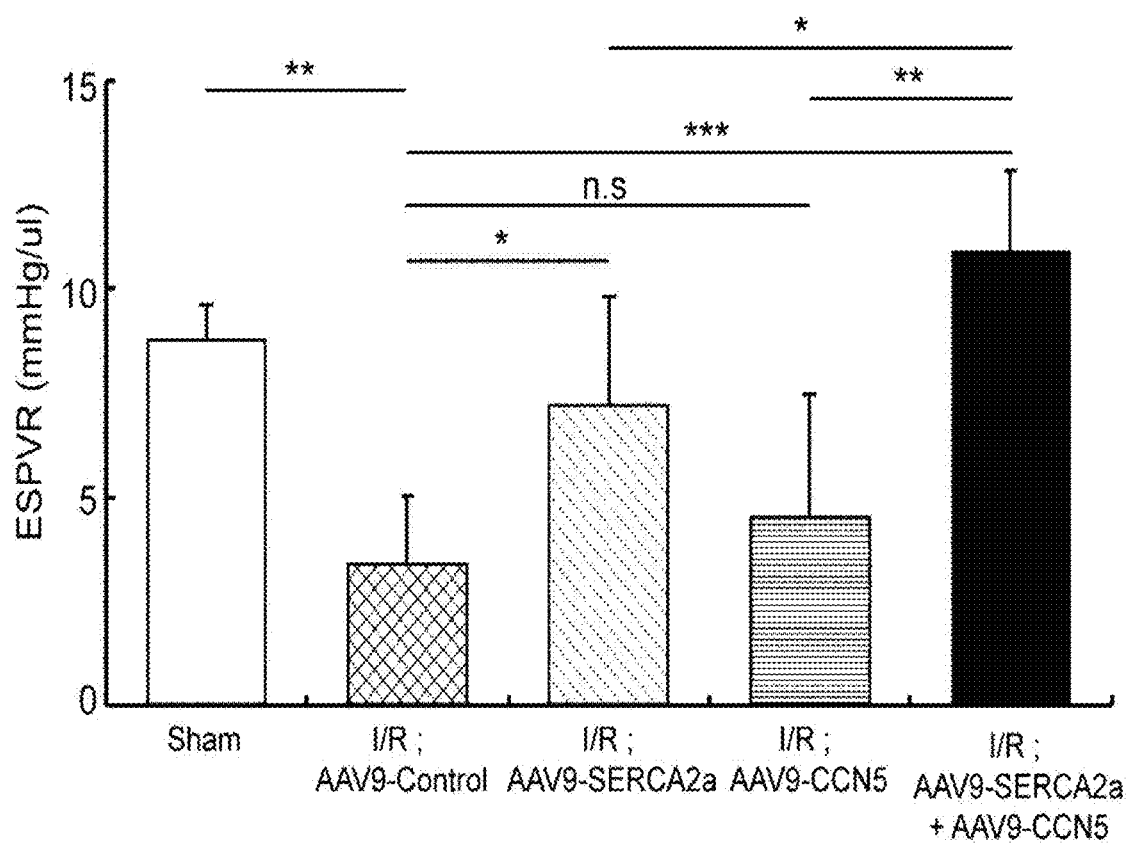

[Fig. 9b]
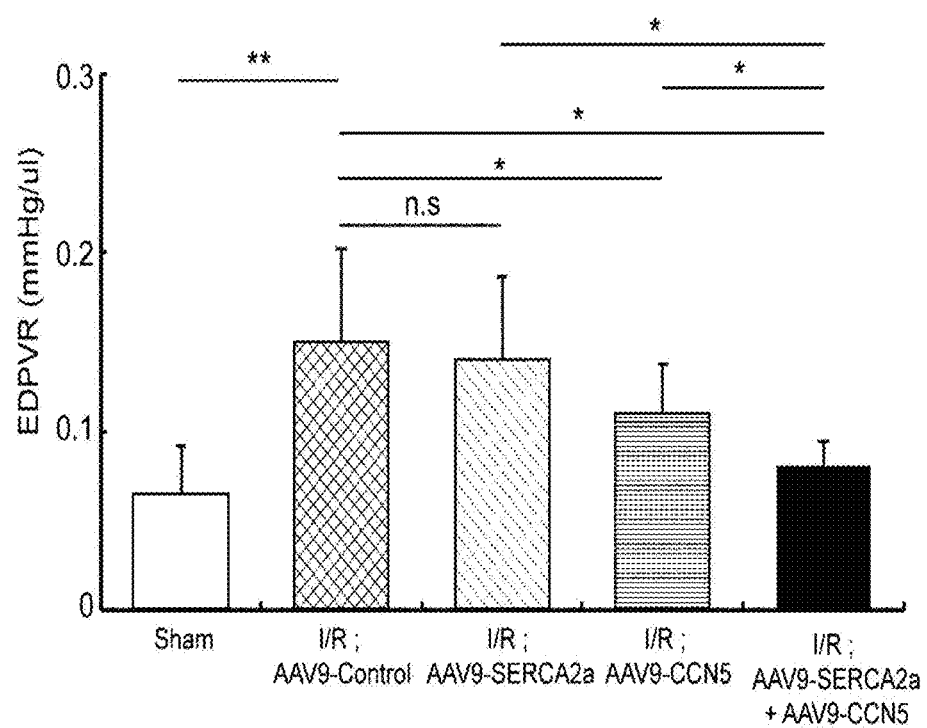

[Fig. 10]
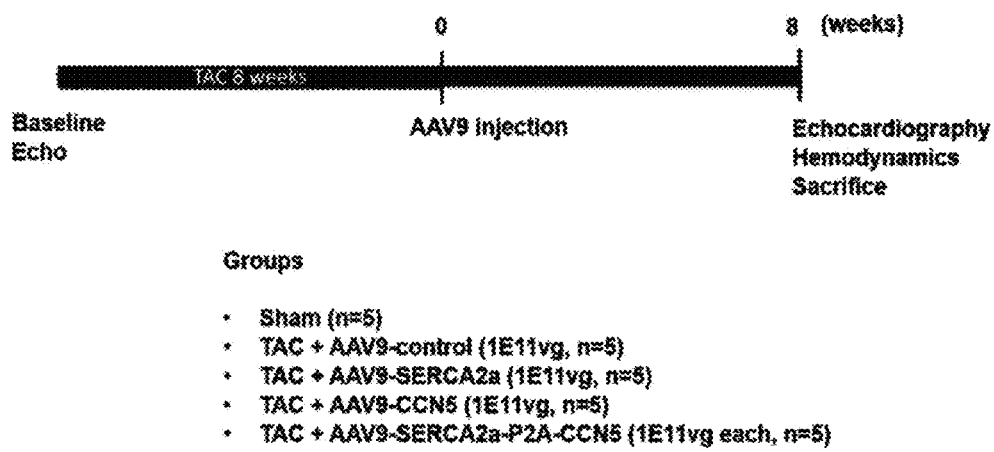
Groups
- Sham (n=5)
- TAC + AAV9-control (1E11vg, n=5)
- TAC + AAV9-SERCA2a (1E11vg, n=5)
- TAC + AAV9-CCN5 (1E11vg, n=5)
- TAC + AAV9-SERCA2a-P2A-CCN5 (1E11vg each, n=5)
Method
- TAC for 2 months, FS(%) was confirmed by Echo and less than 50% mice were used for experiments
- Injection method : tail vein injection 8 weeks after TAC

[Fig. 11a]
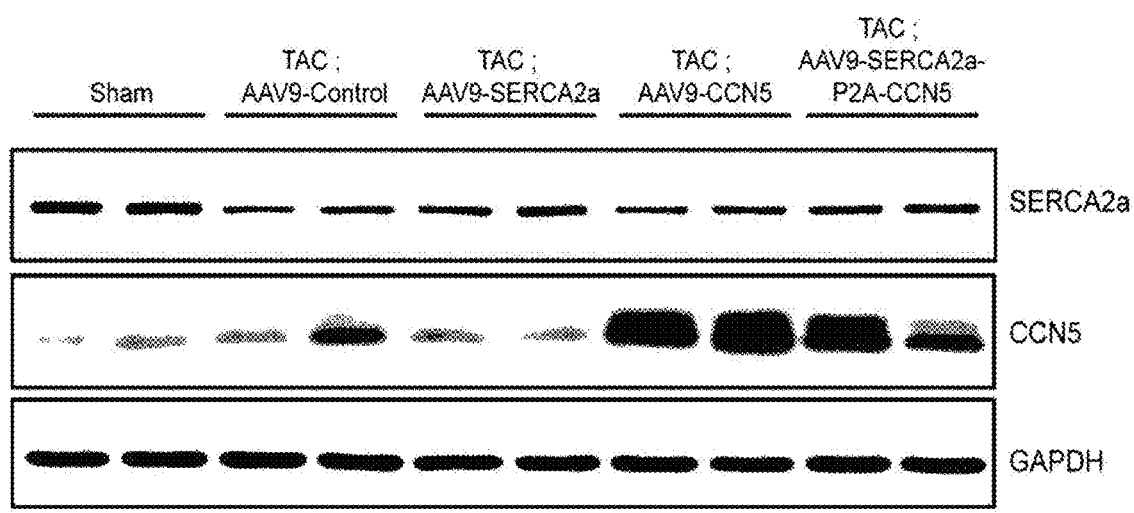

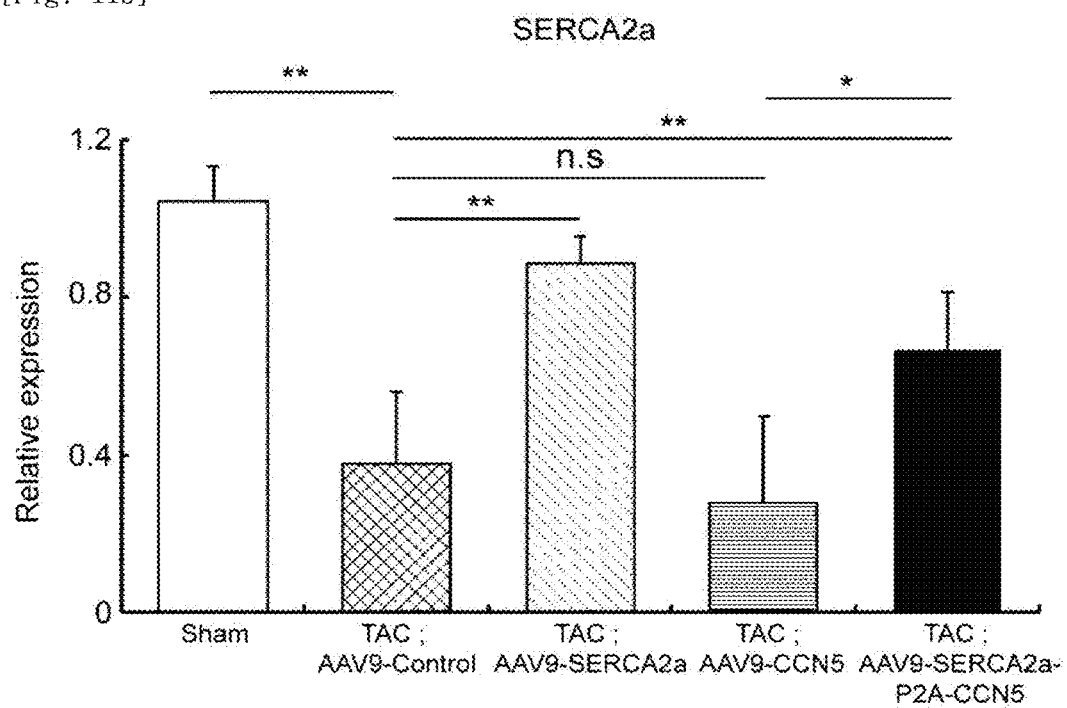
[Fig. 11b]

[Fig. 11c]
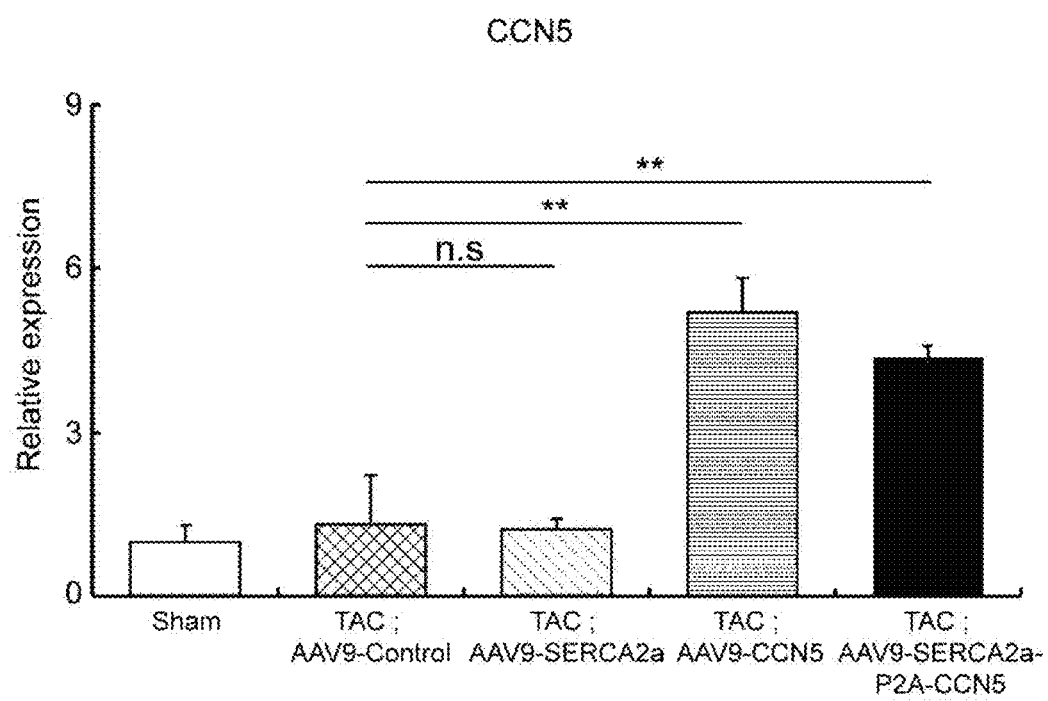

[Fig. 12]
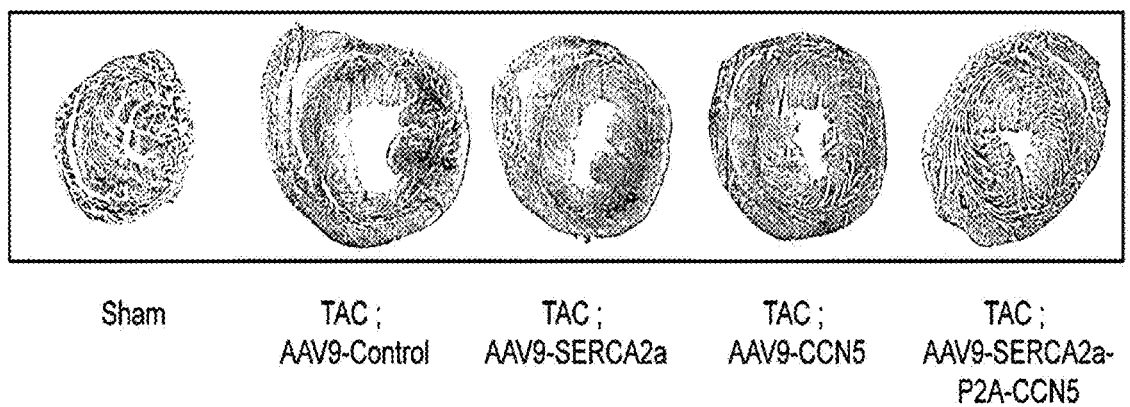

[Fig. 13]
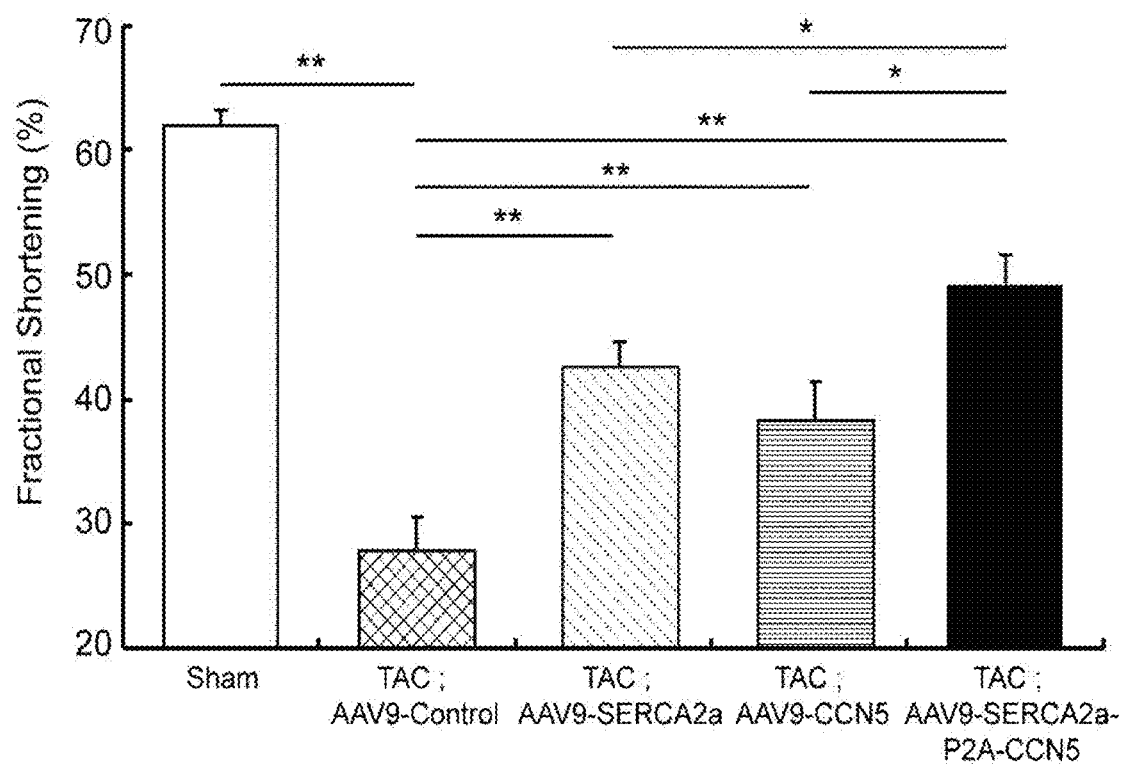

[Fig. 14a]
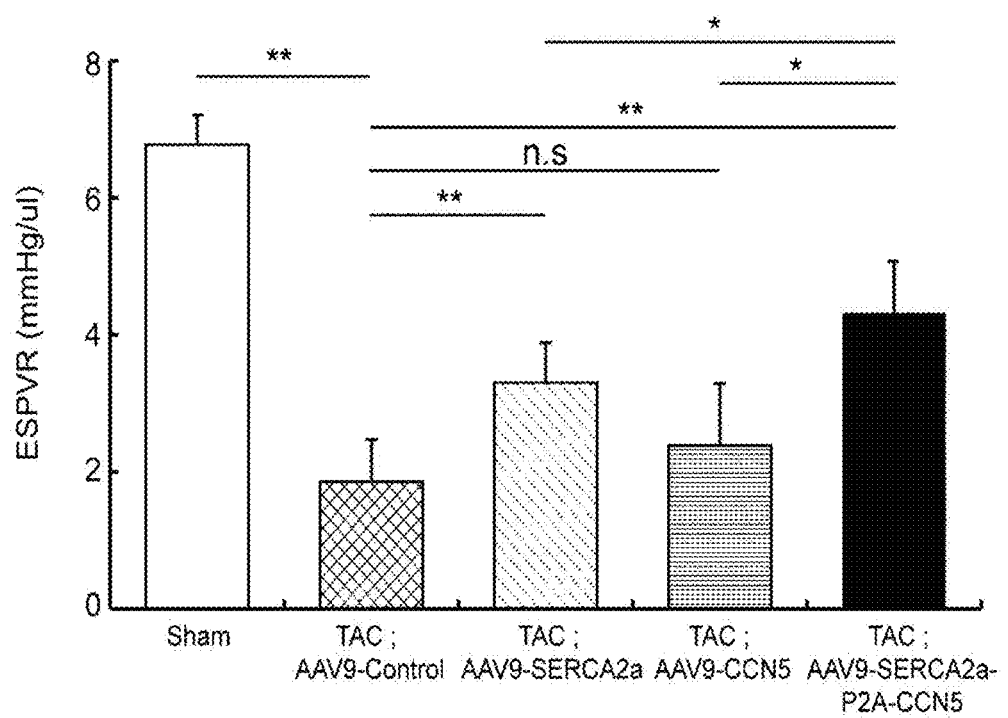

[Fig. 14b]
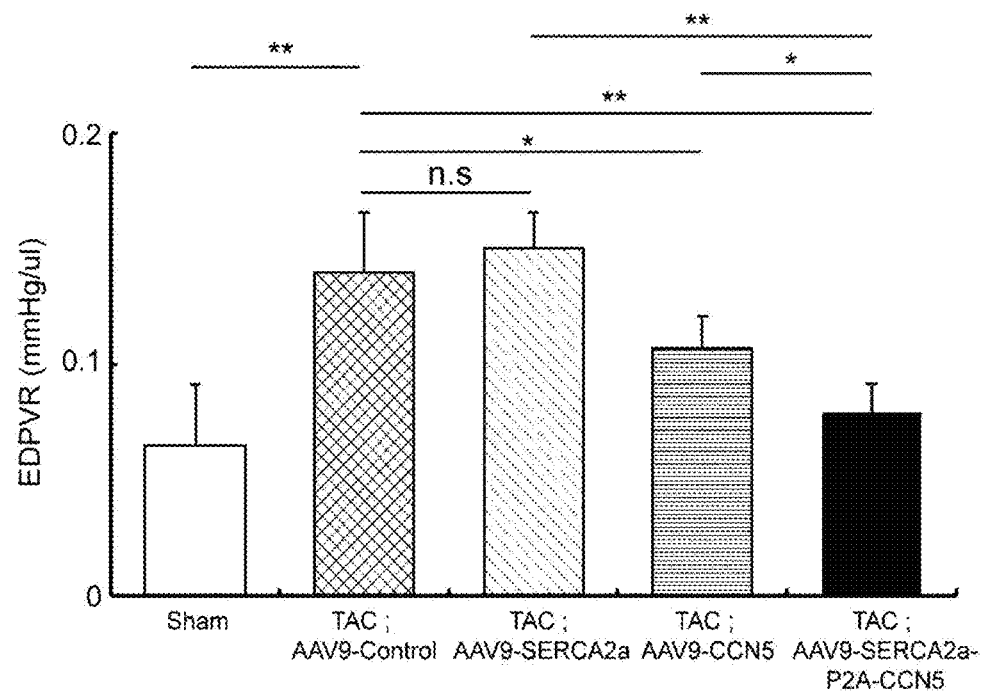

[Fig. 15]

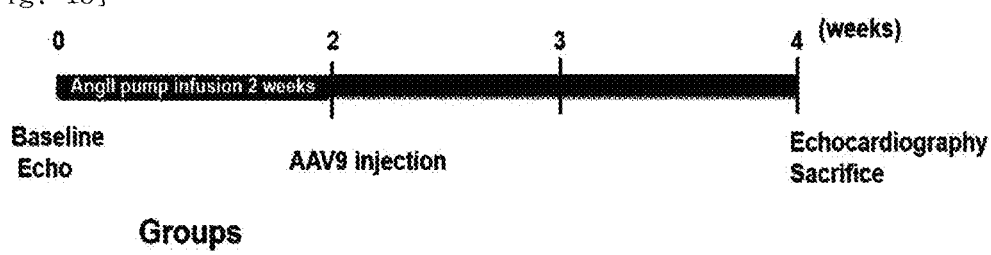

Groups

- Sham (n=3)
- AngII + AAV9-control (5E11vg, n=5)
- AngII + AAV9-SERCA2a (5E11vg, n=5)
- AngII + AAV9-CCN5 (5E11vg, n=5)
- AngII + AAV9-SERCA2a-P2A-CCN5 (5E11vg, n=5)

Materials and Methods

- Mouse strain: B6C3F1 (gray mouse)
- Infusion material: micro-osmotic pump model 1002 - ALZET® Osmotic Pumps (subcutaneously infused on the back of mice)
- AngII (2mg/kg) infusion for 2 weeks
- Gene therapy : Intravenous injection via tail vein at 2 weeks after AngII infusion

[Fig. 16a]
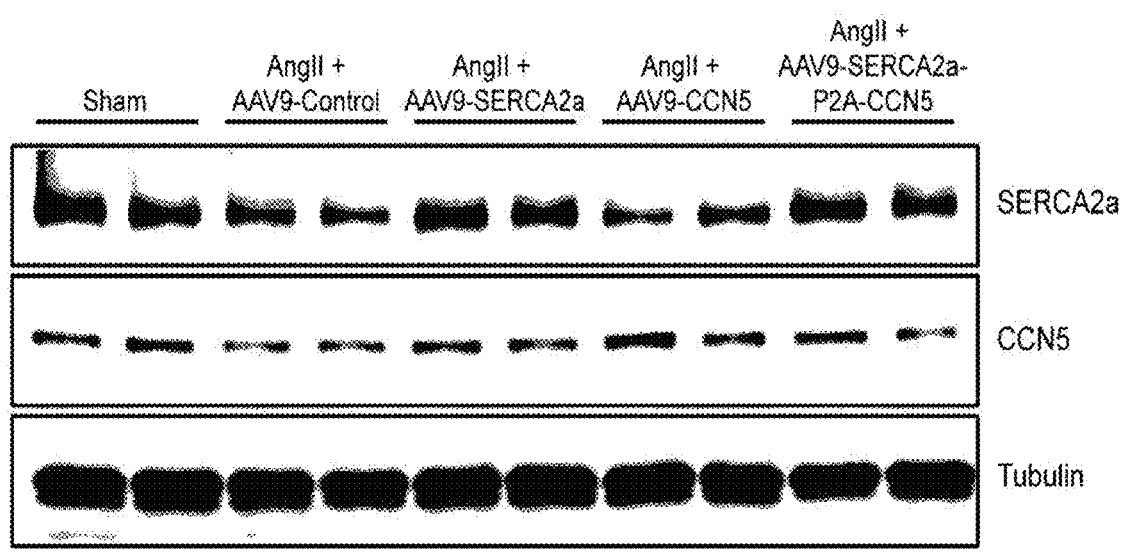

[Fig. 16b]
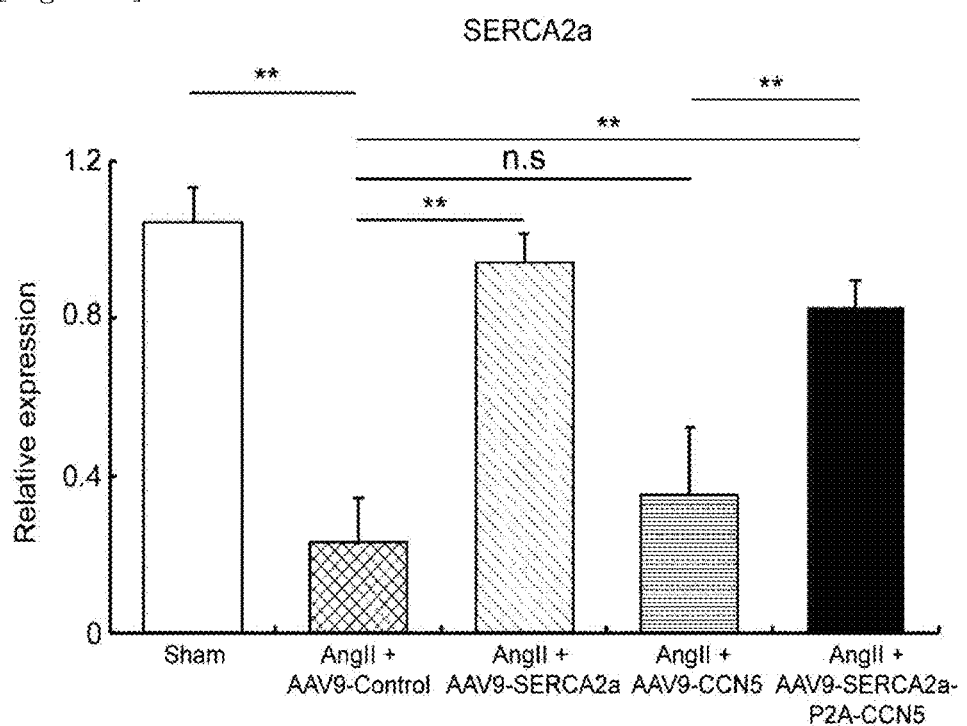

[Fig. 16c]
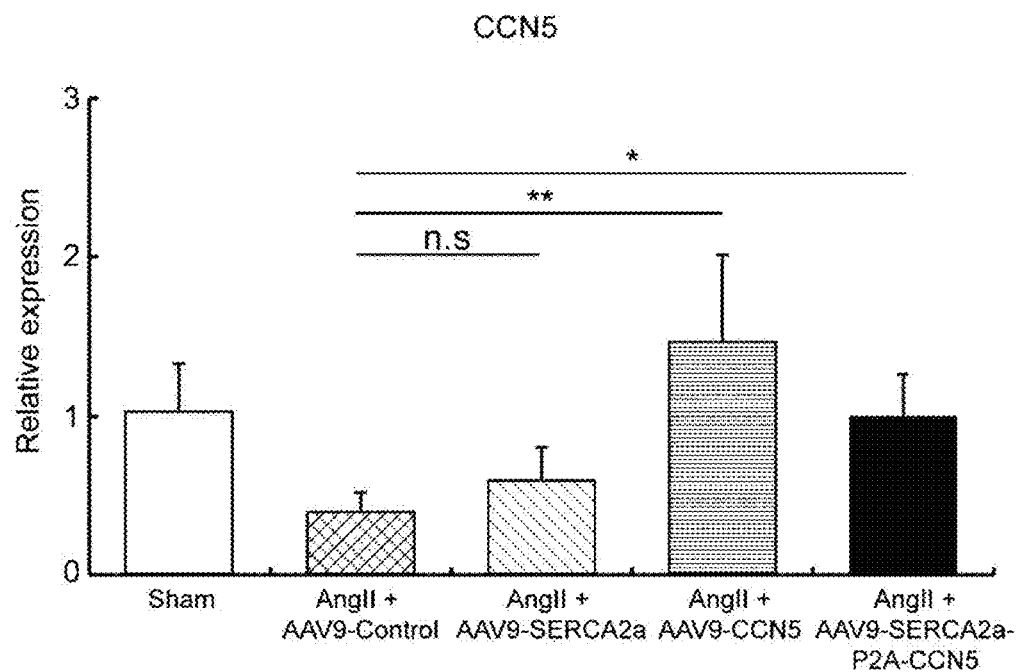

[Fig. 17]
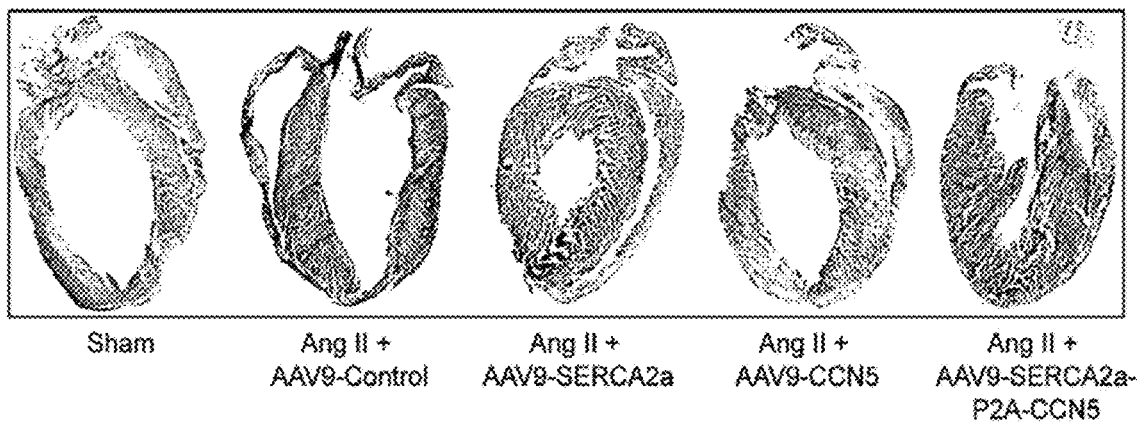

[Fig. 18]
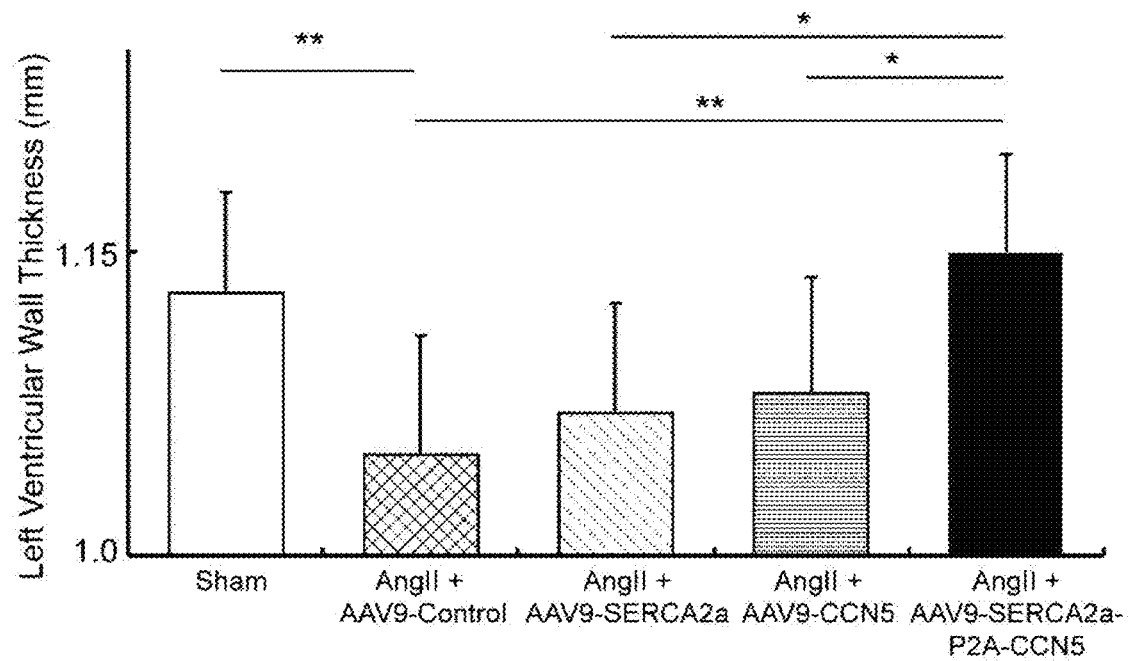

[Fig. 19]
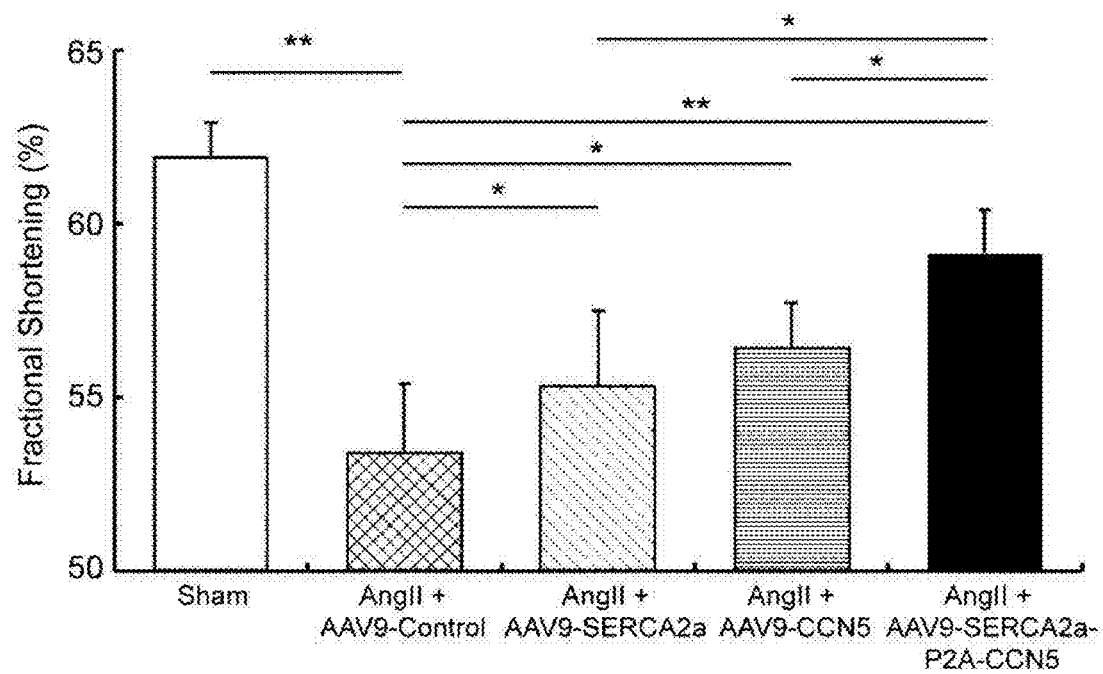

SEQUENCE LISTING

```
<160> NUMBER OF SEQ ID NOS: 14

<210> SEQ ID NO 1
<211> LENGTH: 997
<212> TYPE: PRT
<213> ORGANISM: Homo sapiens

<400> SEQUENCE: 1

Met Glu Asn Ala His Thr Lys Thr Val Glu Glu Val Leu Gly His Phe
1               5                   10                  15

Gly Val Asn Glu Ser Thr Gly Leu Ser Leu Glu Gln Val Lys Lys Leu
            20                  25                  30

Lys Glu Arg Trp Gly Ser Asn Glu Leu Pro Ala Glu Glu Gly Lys Thr
        35                  40                  45

Leu Leu Glu Leu Val Ile Glu Gln Phe Glu Asp Leu Leu Val Arg Ile
    50                  55                  60

Leu Leu Leu Ala Ala Cys Ile Ser Phe Val Leu Ala Trp Phe Glu Glu
65                  70                  75                  80

Gly Glu Glu Thr Ile Thr Ala Phe Val Glu Pro Phe Val Ile Leu Leu
                85                  90                  95

Ile Leu Val Ala Asn Ala Ile Val Gly Val Trp Gln Glu Arg Asn Ala
            100                 105                 110

Glu Asn Ala Ile Glu Ala Leu Lys Glu Tyr Glu Pro Glu Met Gly Lys
        115                 120                 125

Val Tyr Arg Gln Asp Arg Lys Ser Val Gln Arg Ile Lys Ala Lys Asp
    130                 135                 140

Ile Val Pro Gly Asp Ile Val Glu Ile Ala Val Gly Asp Lys Val Pro
145                 150                 155                 160

Ala Asp Ile Arg Leu Thr Ser Ile Lys Ser Thr Thr Leu Arg Val Asp
                165                 170                 175

Gln Ser Ile Leu Thr Gly Glu Ser Val Ser Val Ile Lys His Thr Asp
            180                 185                 190

Pro Val Pro Asp Pro Arg Ala Val Asn Gln Asp Lys Lys Asn Met Leu
        195                 200                 205

Phe Ser Gly Thr Asn Ile Ala Ala Gly Lys Ala Met Gly Val Val Val
    210                 215                 220

Ala Thr Gly Val Asn Thr Glu Ile Gly Lys Ile Arg Asp Glu Met Val
```

```
            225                 230                 235                 240
Ala Thr Glu Gln Glu Arg Thr Pro Leu Gln Gln Lys Leu Asp Glu Phe
                    245                 250                 255

Gly Glu Gln Leu Ser Lys Val Ile Ser Leu Ile Cys Ile Ala Val Trp
            260                 265                 270

Ile Ile Asn Ile Gly His Phe Asn Asp Pro Val His Gly Gly Ser Trp
                275                 280                 285

Ile Arg Gly Ala Ile Tyr Tyr Phe Lys Ile Ala Val Ala Leu Ala Val
        290                 295                 300

Ala Ala Ile Pro Glu Gly Leu Pro Ala Val Ile Thr Thr Cys Leu Ala
305                 310                 315                 320

Leu Gly Thr Arg Arg Met Ala Lys Lys Asn Ala Ile Val Arg Ser Leu
                325                 330                 335

Pro Ser Val Glu Thr Leu Gly Cys Thr Ser Val Ile Cys Ser Asp Lys
            340                 345                 350

Thr Gly Thr Leu Thr Thr Asn Gln Met Ser Val Cys Arg Met Phe Ile
                355                 360                 365

Leu Asp Arg Val Glu Gly Asp Thr Cys Ser Leu Asn Glu Phe Thr Ile
        370                 375                 380

Thr Gly Ser Thr Tyr Ala Pro Ile Gly Glu Val His Lys Asp Asp Lys
385                 390                 395                 400

Pro Val Asn Cys His Gln Tyr Asp Gly Leu Val Glu Leu Ala Thr Ile
                405                 410                 415

Cys Ala Leu Cys Asn Asp Ser Ala Leu Asp Tyr Asn Glu Ala Lys Gly
            420                 425                 430

Val Tyr Glu Lys Val Gly Glu Ala Thr Glu Thr Ala Leu Thr Cys Leu
        435                 440                 445

Val Glu Lys Met Asn Val Phe Asp Thr Glu Leu Lys Gly Leu Ser Lys
        450                 455                 460

Ile Glu Arg Ala Asn Ala Cys Asn Ser Val Ile Lys Gln Leu Met Lys
465                 470                 475                 480

Lys Glu Phe Thr Leu Glu Phe Ser Arg Asp Arg Lys Ser Met Ser Val
                485                 490                 495

Tyr Cys Thr Pro Asn Lys Pro Ser Arg Thr Ser Met Ser Lys Met Phe
            500                 505                 510

Val Lys Gly Ala Pro Glu Gly Val Ile Asp Arg Cys Thr His Ile Arg
            515                 520                 525

Val Gly Ser Thr Lys Val Pro Met Thr Ser Gly Val Lys Gln Lys Ile
        530                 535                 540

Met Ser Val Ile Arg Glu Trp Gly Ser Gly Ser Asp Thr Leu Arg Cys
545                 550                 555                 560

Leu Ala Leu Ala Thr His Asp Asn Pro Leu Arg Arg Glu Glu Met His
                565                 570                 575

Leu Glu Asp Ser Ala Asn Phe Ile Lys Tyr Glu Thr Asn Leu Thr Phe
            580                 585                 590

Val Gly Cys Val Gly Met Leu Asp Pro Pro Arg Ile Glu Val Ala Ser
        595                 600                 605

Ser Val Lys Leu Cys Arg Gln Ala Gly Ile Arg Val Ile Met Ile Thr
        610                 615                 620

Gly Asp Asn Lys Gly Thr Ala Val Ala Ile Cys Arg Arg Ile Gly Ile
625                 630                 635                 640

Phe Gly Gln Asp Glu Asp Val Thr Ser Lys Ala Phe Thr Gly Arg Glu
                645                 650                 655
```

-continued

```
Phe Asp Glu Leu Asn Pro Ser Ala Gln Arg Asp Ala Cys Leu Asn Ala
            660                 665                 670

Arg Cys Phe Ala Arg Val Glu Pro Ser His Lys Ser Lys Ile Val Glu
        675                 680                 685

Phe Leu Gln Ser Phe Asp Glu Ile Thr Ala Met Thr Gly Asp Gly Val
    690                 695                 700

Asn Asp Ala Pro Ala Leu Lys Lys Ala Glu Ile Gly Ile Ala Met Gly
705                 710                 715                 720

Ser Gly Thr Ala Val Ala Lys Thr Ala Ser Glu Met Val Leu Ala Asp
                725                 730                 735

Asp Asn Phe Ser Thr Ile Val Ala Ala Val Glu Glu Gly Arg Ala Ile
            740                 745                 750

Tyr Asn Asn Met Lys Gln Phe Ile Arg Tyr Leu Ile Ser Ser Asn Val
        755                 760                 765

Gly Glu Val Val Cys Ile Phe Leu Thr Ala Ala Leu Gly Phe Pro Glu
    770                 775                 780

Ala Leu Ile Pro Val Gln Leu Leu Trp Val Asn Leu Val Thr Asp Gly
785                 790                 795                 800

Leu Pro Ala Thr Ala Leu Gly Phe Asn Pro Pro Asp Leu Asp Ile Met
                805                 810                 815

Asn Lys Pro Pro Arg Asn Pro Lys Glu Pro Leu Ile Ser Gly Trp Leu
            820                 825                 830

Phe Phe Arg Tyr Leu Ala Ile Gly Cys Tyr Val Gly Ala Ala Thr Val
        835                 840                 845

Gly Ala Ala Ala Trp Trp Phe Ile Ala Ala Asp Gly Gly Pro Arg Val
    850                 855                 860

Ser Phe Tyr Gln Leu Ser His Phe Leu Gln Cys Lys Glu Asp Asn Pro
865                 870                 875                 880

Asp Phe Glu Gly Val Asp Cys Ala Ile Phe Glu Ser Pro Tyr Pro Met
                885                 890                 895

Thr Met Ala Leu Ser Val Leu Val Thr Ile Glu Met Cys Asn Ala Leu
            900                 905                 910

Asn Ser Leu Ser Glu Asn Gln Ser Leu Leu Arg Met Pro Pro Trp Glu
        915                 920                 925

Asn Ile Trp Leu Val Gly Ser Ile Cys Leu Ser Met Ser Leu His Phe
    930                 935                 940

Leu Ile Leu Tyr Val Glu Pro Leu Pro Leu Ile Phe Gln Ile Thr Pro
945                 950                 955                 960

Leu Asn Val Thr Gln Trp Leu Met Val Leu Lys Ile Ser Leu Pro Val
                965                 970                 975

Ile Leu Met Asp Glu Thr Leu Lys Phe Val Ala Arg Asn Tyr Leu Glu
            980                 985                 990

Pro Ala Ile Leu Glu
        995

<210> SEQ ID NO 2
<211> LENGTH: 2991
<212> TYPE: DNA
<213> ORGANISM: Homo sapiens

<400> SEQUENCE: 2
atggagaacg cgcacaccaa gacggtggag gaggtgctgg gccacttcgg cgtcaacgag      60 agtacgggc tgagcctgga acaggtcaag aagcttaagg agagatgggg ctccaacgag     120
```

```
ttaccggctg aagaaggaaa aaccttgctg gaacttgtga ttgagcagtt tgaagacttg      180
ctagttagga ttttattact ggcagcatgt atatcttttg ttttggcttg gtttgaagaa      240
ggtgaagaaa caattacagc ctttgtagaa ccttttgtaa ttttactcat attagtagcc      300
aatgcaattg tgggtgtatg gcaggaaaga aatgctgaaa atgccatcga agcccttaag      360
gaatatgagc ctgaaatggg caaagtgtat cgacaggaca gaaagagtgt gcagcggatt      420
aaagctaaag acatagttcc tggtgatatt gtagaaattg ctgttggtga caaagttcct      480
gctgatataa ggttaacttc catcaaatct accacactaa gagttgacca gtcaattctc      540
acaggtgaat ctgtctctgt catcaagcac actgatcccg tccctgaccc acagctgtc       600 aaccaagata aaagaacat gctgttttct ggtacaaaca ttgctgctgg gaaagctatg        660
ggagtggtgg tagcaactgg agttaacacc gaaattggca agatccggga tgaaatggtg      720
gcaacagaac aggagagaac acccctccag caaaaactag atgaatttgg ggaacagctt      780
tccaaagtca tctcccttat ttgcattgca gtctggatca taaatattgg gcacttcaat      840
gacccggttc atggagggtc ctggatcaga ggtgctattt actactttaa aattgcagtg      900
gccctggctg tagcagccat tcctgaaggt ctgcctgcag tcatcaccac ctgcctggct      960 cttgaactc gcagaatggc aaagaaaaat gccattgttc gaagcctccc gtctgtggaa      1020
acccttggtt gtacttctgt tatctgctca gacaagactg gtacacttac aacaaaccag      1080
atgtcagtct gcaggatgtt cattctggac agagtggaag gtgatacttg ttcccttaat      1140
gagtttacca taactggatc aacttatgca cctattggag aagtgcataa agatgataaa      1200
ccagtgaatt gtcaccagta tgatggtctg gtagaattag caacaattg tgctctttgt       1260 aatgactctg ctttggatta caatgaggca agggtgtgt atgaaaaagt tggagaagct      1320
acagagactg ctctcacttg cctagtagag aagatgaatg tatttgatac cgaattgaag      1380
ggtctttcta aaatagaacg tgcaaatgcc tgcaactcag tcattaaaca gctgatgaaa      1440
aaggaattca ctctagagtt ttcacgtgac agaaagtcaa tgtcggttta ctgtacacca      1500
aataaaccaa gcaggacatc aatgagcaag atgtttgtga agggtgctcc tgaaggtgtc      1560
attgacaggt gcacccacat tcgagttgga agtactaagg ttcctatgac ctctggagtc      1620
aaacagaaga tcatgtctgt cattcgagag tggggtagtg gcagcgacac actgcgatgc      1680
ctggccctgg ccactcatga caacccactg agaagagaag aaatgcacct tgaggactct      1740
gccaacttta ttaaatatga gaccaatctg accttcgttg gctgcgtggg catgctggat      1800
cctccgagaa tcgaggtggc ctcctccgtg aagctgtgcc ggcaagcagg catccgggtc      1860
atcatgatca ctggggacaa caagggcact gctgtggcca tctgtcgccg catcggcatc      1920
ttcgggcagg atgaggacgt gacgtcaaaa gctttcacag gccgggagtt tgatgaactc      1980
aacccctccg cccagcgaga cgcctgcctg aacgcccgct gttttgctcg agttgaaccc      2040
tcccacaagt ctaaaatcgt agaatttctt cagtcttttg atgagattac agctatgact      2100
ggcgatggcg tgaacgatgc tcctgctctg aagaaagccg agattggcat tgctatgggc      2160
tctggcactg cggtggctaa aaccgcctct gagatggtcc tggcggatga caacttctcc      2220
accattgtgg ctgccgttga ggaggggcgg gcaatctaca acaacatgaa acagttcatc      2280
cgctacctca tctcgtccaa cgtcgggaa gttgtctgta ttttcctgac agcagccctt      2340 ggattcccg aggcttttga tcctgttcag ctgctctggg tcaatctggt gacagatggc      2400
ctgcctgcca ctgcactggg gttcaaccct cctgatctgg acatcatgaa taaacctccc      2460
cggaacccaa aggaaccatt gatcagcggg tggctctttt tccgttactt ggctattggc      2520
```

```
tgttacgtcg gcgctgctac cgtgggtgct gctgcatggt ggttcattgc tgctgacggt    2580
ggtccaagag tgtccttcta ccagctgagt catttcctac agtgtaaaga ggacaacccg    2640
gactttgaag gcgtggattg tgcaatcttt gaatccccat acccgatgac aatggcgctc    2700
tctgttctag taactataga aatgtgtaac gccctcaaca gcttgtccga aaaccagtcc    2760
ttgctgagga tgccccctg ggagaacatc tggctcgtgg gctccatctg cctgtccatg    2820
tcactccact tcctgatcct ctatgtcgaa cccttgccac tcatcttcca gatcacaccg    2880
ctgaacgtga cccagtggct gatggtgctg aaaatctcct gcccgtgat tctcatggat    2940 gagacgctca agtttgtggc ccgcaactac ctggaacctg caatactgga g            2991
```

<210> SEQ ID NO 3
<211> LENGTH: 250
<212> TYPE: PRT
<213> ORGANISM: Homo sapiens

<400> SEQUENCE: 3

```
Met Arg Gly Thr Pro Lys Thr His Leu Leu Ala Phe Ser Leu Leu Cys
1               5                   10                  15

Leu Leu Ser Lys Val Arg Thr Gln Leu Cys Pro Thr Pro Cys Thr Cys
            20                  25                  30

Pro Trp Pro Pro Pro Arg Cys Pro Leu Gly Val Pro Leu Val Leu Asp
        35                  40                  45

Gly Cys Gly Cys Cys Arg Val Cys Ala Arg Arg Leu Gly Glu Pro Cys
    50                  55                  60

Asp Gln Leu His Val Cys Asp Ala Ser Gln Gly Leu Val Cys Gln Pro
65                  70                  75                  80

Gly Ala Gly Pro Gly Gly Arg Gly Ala Leu Cys Leu Leu Ala Glu Asp
                85                  90                  95

Asp Ser Ser Cys Glu Val Asn Gly Arg Leu Tyr Arg Glu Gly Glu Thr
            100                 105                 110

Phe Gln Pro His Cys Ser Ile Arg Cys Arg Cys Glu Asp Gly Gly Phe
        115                 120                 125

Thr Cys Val Pro Leu Cys Ser Glu Asp Val Arg Leu Pro Ser Trp Asp
    130                 135                 140

Cys Pro His Pro Arg Arg Val Glu Val Leu Gly Lys Cys Cys Pro Glu
145                 150                 155                 160

Trp Val Cys Gly Gln Gly Gly Gly Leu Gly Thr Gln Pro Leu Pro Ala
                165                 170                 175

Gln Gly Pro Gln Phe Ser Gly Leu Val Ser Ser Leu Pro Pro Gly Val
            180                 185                 190

Pro Cys Pro Glu Trp Ser Thr Ala Trp Gly Pro Cys Ser Thr Thr Cys
        195                 200                 205

Gly Leu Gly Met Ala Thr Arg Val Ser Asn Gln Asn Arg Phe Cys Arg
    210                 215                 220

Leu Glu Thr Gln Arg Arg Leu Cys Leu Ser Arg Pro Cys Pro Pro Ser
225                 230                 235                 240

Arg Gly Arg Ser Pro Gln Asn Ser Ala Phe
                245                 250
```

<210> SEQ ID NO 4
<211> LENGTH: 750
<212> TYPE: DNA
<213> ORGANISM: Homo sapiens

```
<400> SEQUENCE: 4
atgagaggca caccgaagac ccacctcctg gccttctccc tcctctgcct cctctcaaag    60
gtgcgtaccc agctgtgccc gacaccatgt acctgcccct ggccacctcc ccgatgcccg   120
ctgggagtac ccctggtgct ggatggctgt ggctgctgcc gggtatgtgc acggcggctg   180
ggggagccct gcgaccaact ccacgtctgc gacgccagcc agggcctggt ctgccagccc   240
ggggcaggac ccggtggccg gggggccctg tgcctcttgg cagaggacga cagcagctgt   300
gaggtgaacg gccgcctgta tcgggaaggg gagaccttcc agccccactg cagcatccgc   360
tgccgctgcg aggacggcgg cttcacctgc gtgccgctgt gcagcgagga tgtgcggctg   420
cccagctggg actgccccca ccccaggagg gtcgaggtcc tgggcaagtg ctgccctgag   480
tgggtgtgcg gccaaggagg gggactgggg acccagcccc ttccagccca aggaccccag   540
ttttctggcc ttgtctcttc cctgcccctg gtgtccccct gcccagaatg gagcacggcc   600
tggggaccct gctcgaccac ctgtgggctg gcatggcca cccgggtgtc caaccagaac   660
cgcttctgcc gactggagac ccagcgccgc ctgtgcctgt ccaggccctg cccaccctcc   720
aggggtcgca gtccacaaaa cagtgccttc                                    750

<210> SEQ ID NO 5
<211> LENGTH: 22
<212> TYPE: PRT
<213> ORGANISM: Artificial Sequence
<220> FEATURE:
<223> OTHER INFORMATION: self-cleavage sequence derived from porcine
      teschovirus-1

<400> SEQUENCE: 5

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 6
<211> LENGTH: 66
<212> TYPE: DNA
<213> ORGANISM: Artificial Sequence
<220> FEATURE:
<223> OTHER INFORMATION: self-cleavage sequence derived from porcine
      teschovirus-1

<400> SEQUENCE: 6
ggaagcggag ctactaactt cagcctgctg aagcaggctg agacgtggga ggagaaccct    60
ggacct                                                              66

<210> SEQ ID NO 7
<211> LENGTH: 21
<212> TYPE: PRT
<213> ORGANISM: Artificial Sequence
<220> FEATURE:
<223> OTHER INFORMATION: self-cleavage sequence derived from
      Thoseaasigna virus

<400> SEQUENCE: 7

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 8
```

```
<211> LENGTH: 63
<212> TYPE: DNA
<213> ORGANISM: Artificial Sequence
<220> FEATURE:
<223> OTHER INFORMATION: self-cleavage sequence derived from
      Thoseaasigna virus

<400> SEQUENCE: 8
ggaagcggag agggcagagg aagtctgcta acatgcggtg acgtcgagga gaatcctgga      60
cct                                                                    63

<210> SEQ ID NO 9
<211> LENGTH: 23
<212> TYPE: PRT
<213> ORGANISM: Artificial Sequence
<220> FEATURE:
<223> OTHER INFORMATION: self-cleavage sequence derived from equine
      rhinitis A virus (ERAV)

<400> SEQUENCE: 9

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 10
<211> LENGTH: 69
<212> TYPE: DNA
<213> ORGANISM: Artificial Sequence
<220> FEATURE:
<223> OTHER INFORMATION: self-cleavage sequence derived from equine
      rhinitis A virus (ERAV)

<400> SEQUENCE: 10
ggaagcggac agtgtactaa ttatgctctc ttgaaattgg ctggagatgt tgagagcaac      60
cctggacct                                                              69

<210> SEQ ID NO 11
<211> LENGTH: 25
<212> TYPE: PRT
<213> ORGANISM: Artificial Sequence
<220> FEATURE:
<223> OTHER INFORMATION: self-cleavage sequence derived from FMDV 2A

<400> SEQUENCE: 11

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 12
<211> LENGTH: 75
<212> TYPE: DNA
<213> ORGANISM: Artificial Sequence
<220> FEATURE:
<223> OTHER INFORMATION: self-cleavage sequence derived from FMDV 2A

<400> SEQUENCE: 12
ggaagcggag tgaaacagac tttgaatttt gaccttctca gttggcggg agacgtggag       60 tccaaccctg gacct                                                       75

<210> SEQ ID NO 13
<211> LENGTH: 2994
<212> TYPE: DNA
```

<213> ORGANISM: Homo sapiens

<400> SEQUENCE: 13

| | | | | | |
|---|---|---|---|---|---|
| atggagaacg | cgcacaccaa | gacggtggag | gaggtgctgg | gccacttcgg | cgtcaacgag | 60 |
| agtacgggc | tgagcctgga | acaggtcaag | aagcttaagg | agagatgggg | ctccaacgag | 120 |
| ttaccggctg | aagaaggaaa | aaccttgctg | gaacttgtga | ttgagcagtt | tgaagacttg | 180 |
| ctagttagga | ttttattact | ggcagcatgt | atatcttttg | ttttggcttg | gtttgaagaa | 240 |
| ggtgaagaaa | caattacagc | cttttgtagaa | ccttttgtaa | ttttactcat | attagtagcc | 300 |
| aatgcaattg | tgggtgtatg | gcaggaaaga | aatgctgaaa | atgccatcga | agcccttaag | 360 |
| gaatatgagc | ctgaaatggg | caaagtgtat | cgacaggaca | gaaagagtgt | gcagcggatt | 420 |
| aaagctaaag | acatagttcc | tggtgatatt | gtagaaattg | ctgttggtga | caaagttcct | 480 |
| gctgatataa | ggttaacttc | catcaaatct | accacactaa | gagttgacca | gtcaattctc | 540 |
| acaggtgaat | ctgtctctgt | catcaagcac | actgatcccg | tccctgaccc | acgagctgtc | 600 |
| aaccaagata | aaagaacat | gctgttttct | ggtacaaaca | ttgctgctgg | gaaagctatg | 660 |
| ggagtggtgg | tagcaactgg | agttaacacc | gaaattggca | agatccggga | tgaaatggtg | 720 |
| gcaacagaac | aggagagaac | accccttcag | caaaaactag | atgaatttgg | ggaacagctt | 780 |
| tccaaagtca | tctcccttat | ttgcattgca | gtctggatca | taaatattgg | gcacttcaat | 840 |
| gacccggttc | atgagggtc | ctggatcaga | ggtgctattt | actactttaa | aattgcagtg | 900 |
| gccctggctg | tagcagccat | tcctgaaggt | ctgcctgcag | tcatcaccac | ctgcctggct | 960 |
| cttggaactc | gcagaatggc | aaagaaaaat | gccattgttc | gaagcctccc | gtctgtggaa | 1020 |
| acccttggtt | gtacttctgt | tatctgctca | gacaagactg | gtacacttac | aacaaaccag | 1080 |
| atgtcagtct | gcaggatgtt | cattctggac | agagtggaag | gtgatacttg | ttcccttaat | 1140 |
| gagtttacca | taactggatc | aacttatgca | cctattggag | aagtgcataa | agatgataaa | 1200 |
| ccagtgaatt | gtcaccagta | tgatggtctg | gtagaattag | caacaatttg | tgctctttgt | 1260 |
| aatgactctg | ctttggatta | caatgaggca | aagggtgtgt | atgaaaaagt | tggagaagct | 1320 |
| acagagactg | ctctcacttg | cctagtagag | aagatgaatg | tatttgatac | cgaattgaag | 1380 |
| ggtctttcta | aaatagaacg | tgcaaatgcc | tgcaactcag | tcattaaaca | gctgatgaaa | 1440 |
| aaggaattca | ctctagagtt | ttcacgtgac | agaaagtcaa | tgtcggttta | ctgtacacca | 1500 |
| aataaaccaa | gcaggacatc | aatgagcaag | atgtttgtga | agggtgctcc | tgaaggtgtc | 1560 |
| attgacaggt | gcacccacat | tcgagttgga | agtactaagg | ttcctatgac | ctctggagtc | 1620 |
| aaacagaaga | tcatgtctgt | cattcgagag | tggggtagtg | gcagcgacac | actgcgatgc | 1680 |
| ctggccctgg | ccactcatga | caacccactg | agaagagaag | aaatgcacct | tgaggactct | 1740 |
| gccaacttta | ttaaatatga | gaccaatctg | accttcgttg | gctgcgtggg | catgctggat | 1800 |
| cctcgagaa | tcgaggtggc | ctcctccgtg | aagctgtgcc | ggcaagcagg | catccgggtc | 1860 |
| atcatgatca | ctggggacaa | caagggcact | gctgtggcca | tctgtcgccg | catcggcatc | 1920 |
| ttcgggcagg | atgaggacgt | gacgtcaaaa | gctttcacag | gccgggagtt | tgatgaactc | 1980 |
| aaccccctccg | cccagcgaga | cgcctgcctg | aacgcccgct | gttttgctcg | agttgaaccc | 2040 |
| tcccacaagt | ctaaaatcgt | agaatttctt | cagtcttttg | atgagattac | agctatgact | 2100 |
| ggcgatggcg | tgaacgatgc | tcctgctctg | aagaaagccg | agattggcat | tgctatgggc | 2160 |
| tctggcactg | cggtggctaa | aaccgcctct | gagatggtcc | tggcggatga | caacttctcc | 2220 |
| accattgtgg | ctgccgttga | ggaggggcgg | gcaatctaca | caacatgaa | acagttcatc | 2280 |

```
cgctacctca tctcgtccaa cgtcggggaa gttgtctgta ttttcctgac agcagccctt    2340
ggatttcccg aggctttgat tcctgttcag ctgctctggg tcaatctggt gacagatggc    2400
ctgcctgcca ctgcactggg gttcaaccct cctgatctgg acatcatgaa taaacctccc    2460
cggaacccaa aggaaccatt gatcagcggg tggctctttt tccgttactt ggctattggc    2520
tgttacgtcg gcgctgctac cgtgggtgct gctgcatggt ggttcattgc tgctgacggt    2580
ggtccaagag tgtccttcta ccagctgagt catttcctac agtgtaaaga ggacaacccg    2640
gactttgaag gcgtggattg tgcaatcttt gaatccccat acccgatgac aatggcgctc    2700
tctgttctag taactataga aatgtgtaac gccctcaaca gcttgtccga aaaccagtcc    2760
ttgctgagga tgccccctg ggagaacatc tggctcgtgg gctccatctg cctgtccatg    2820
tcactccact tcctgatcct ctatgtcgaa cccttgccac tcatcttcca gatcacaccg    2880
ctgaacgtga cccagtggct gatggtgctg aaaatctcct gcccgtgat tctcatggat    2940 gagacgctca agtttgtggc ccgcaactac ctggaacctg caatactgga gtag    2994
```

<210> SEQ ID NO 14
<211> LENGTH: 753
<212> TYPE: DNA
<213> ORGANISM: Homo sapiens

<400> SEQUENCE: 14

```
atgagaggca caccgaagac ccacctcctg gccttctccc tcctctgcct cctctcaaag     60
gtgcgtaccc agctgtgccc gacaccatgt acctgcccct ggccacctcc ccgatgcccg    120
ctgggagtac ccctggtgct ggatggctgt ggctgctgcc gggtatgtgc acggcggctg    180
ggggagccct gcgaccaact ccacgtctgc gacgccagcc agggcctggt ctgccagccc    240
ggggcaggac ccggtggccg gggggccctg tgcctcttgg cagaggacga cagcagctgt    300
gaggtgaacg gccgcctgta tcgggaaggg gagaccttcc agccccactg cagcatccgc    360
tgccgctgcg aggacggcgg cttcacctgc gtgccgctgt gcagcgagga tgtgcggctg    420
cccagctggg actgccccca ccccaggagg gtcgaggtcc tgggcaagtg ctgccctgag    480
tgggtgtgcg gccaaggagg gggactgggg acccagcccc ttccagccca aggaccccag    540
ttttctggcc ttgtctcttc cctgcccct ggtgtcccct gcccagaatg gagcacggcc    600
tggggaccct gctcgaccac ctgtgggctg gcatggcca cccgggtgtc caaccagaac    660
cgcttctgcc gactggagac ccagcgccgc ctgtgcctgt ccaggccctg cccaccctcc    720
aggggtcgca gtccacaaaa cagtgccttc tag                                 753
```

PHARMACEUTICAL COMPOSITION FOR PREVENTION OR TREATMENT OF HEART FAILURE

CROSS REFERENCE TO RELATED APPLICATIONS

This application is a National Stage of International Application No. PCT/KR2018/011521 filed Sep. 28, 2018, claiming priority based on Korean Patent Application No. 10-2017-0127442 filed Sep. 29, 2017.

INCORPORATION BY REFERENCE OF SEQUENCE LISTING

The content of the electronically submitted sequence listing, file name: Q254042SequenceListingasfiled.txt; size: 23,091 bytes; and date of creation: Mar. 19, 2020, filed herewith, is incorporated herein by reference in its entirety.

TECHNICAL FIELD

The present invention relates to a pharmaceutical composition for preventing or treating heart failure. Specifically, the present invention relates to a gene construct that comprises a nucleotide sequence encoding a SERCA2a protein or a fragment thereof and a nucleotide sequence encoding a CCN5 protein or a fragment thereof, and to a pharmaceutical composition for preventing or treating heart failure which comprises the gene construct as an active ingredient.

BACKGROUND ART

Heart failure (HF) is a disease in which complex symptoms occur due to structural and functional impairment in the ventricular pump function that fills or ejects blood. Heart failure is a disease with a higher mortality rate than cancer, and the mortality rate thereof within 5 years of diagnosis is 50% or higher. The number of heart failure patients is estimated at 38 million people all over the world, and prevalence thereof is also increasing with aging. However, there is no fundamental cure for heart failure, and current treatments can only slow down progression of the disease. Therefore, medical care thereof incurs a lot of treatment costs, which is a big burden on patients (Braunwald E. *Lancet,* 2015; 385: 812-824).

Heart failure is caused by a wide range of heart diseases that result from heart conditions, genetic defects, and systemic diseases. Diseases related to onset of heart failure typically include ischemic, hypertensive, and cardiac valvular diseases, and also include primary cardiomyopathy, secondary cardiomyopathy including amyloidosis, congenital heart diseases, pericardial diseases, and the like, which develop due to genetic or acquired causes (Maron B J. et al., *Circulation.,* 2006; 113: 1807-1816). Heart failure, which develops from various heart diseases, results in pathological cardiac remodeling that leads to structural alteration and dysfunction of the heart. Specifically, regarding the remodeling, there are remodeling at the cellular level, caused by alterations in size, shape, and function of cardiomyocytes, and remodeling at the tissue level, caused by heart tissue fibrosis resulting from excessive accumulation of extracellular matrix (ECM). Such pathological cardiac remodeling involves disease-related changes in transcriptional, signaling, structural, electrophysiological, and functional roles in cardiomyocytes.

The myocardial extracellular matrix (ECM) is a sophisticated structure that supports the mechanical function for efficient contraction and relaxation of cardiomyocytes, and plays a role in facilitating adequate transfer of force, electrical signal transmission, intercellular communication, exchange of metabolites, and the like in a microenvironment within the cardiac muscle. Increased stress, damage, and disease in the heart wall result in progression of fibrosis in the extracellular matrix, thereby causing damage to the motor function, such as contraction and relaxation, of cardiomyocytes and myofibers (Li A H. et al., *Circ Res.,* 2014; 114(5): 916-27).

In addition, pathological remodeling results in dysfunction in contraction and relaxation of the cardiac muscle, and disappearance of cardiomyocytes. Hypertrophy and death of cardiomyocytes at the cellular level affect myocardial excitation-contraction coupling and also result in pathological changes in the molecular mechanism that regulates cardiomyocyte contraction, cell survival, mitochondrial function related to energy metabolism, and oxidative stress (Koitabashi N., et al., *Nat. rev. Cardiol.,* 2012; 9:147-157).

Cardiac tissues undergo pathological structural alterations such as facilitating generation and fibrosis of myofibroblasts, stiffening of vascular smooth muscle, dysfunction in vascular endothelial cells, and inflammatory actions of immune cells. Such disease progression at the cellular level leads to remodeling at the tissue level through integrated processes such as hypertrophy and death of cardiomyocytes, loss of blood vessels, fibrosis, inflammation, metabolic dysfunction, and electrophysiological remodeling, thereby causing heart failure (Burchfield J S et al., *Circulation.* 2013; 128: 388-400).

Neurohormonal blockers have been used for last 40 years as a treatment for heart failure patients. However, despite efficacy of heart failure treatments to relieve symptoms and decrease overload stress in the heart, prognosis of heart failure patients is very poor, with their mortality reaching 50% after 5 years of onset and 90% after 10 years of onset. In addition, in a case where heart failure progresses severely, there is no treatment method other than cardiac assist device and heart transplantation. Therefore, there is an urgent need for development of fundamental cure for heart failure and new therapies to restore the heart.

In relation to new therapies, the areas where development of treatments is actively made in recent years include drugs, cell therapies, miRNAs, and gene therapies, which regulate disease-related signaling systems. Among the above treatments, some drugs have been reported to be effective in animal heart failure disease models or in small-scale phase II clinical trials (Braunwald E. *Lancet,* 2015; 385: 812-824, VonLueder T G. et al., *Nat. Rev. Cardiol.,* 2015; 12: 730-740).

In particular, various preclinical trials for treatment of heart diseases in animals have been conducted by virtue of understanding at the gene level on the disease mechanism of heart diseases, discovery of therapeutic genes, design and packaging techniques for gene vehicles, rapid development of delivery techniques, and the like (Gorski P A, et al. *Cell Metabol.* 2015; 21: 183-194).

In recent years, numerous studies have reported that delivery of SERCA2a gene in heart failure animal models resulted in increased survival rate as well as increased cardiac contractility. However, in a phase IIb clinical trial with a recombinant adeno-associated virus expressing SERCA2a, AAV-SERCA2a, in which a large number of clinical patients as many as 250 participates, gene therapies for heart failure did not show valid clinical benefits unlike the experimental results in pigs, sheep, dogs, and even primates (Rincon M Y et al., *Cardiovas. Res.*, 2015; 108: 4-20).

Even in development of drugs for treatment of heart failure, cases have been reported where new drugs, which have shown a therapeutic effect in phase II clinical trials, show less than expected efficacy or end in failure in phase III clinical trials (Vaduganathan M, et al., *Nat. Rev. Cardiol.*, 2013; 10: 85-97).

Current treatments for heart failure focus on relieving symptoms and decreasing overload stress in the heart. However, despite efficacy of the treatments, prognosis of heart failure patients is very pessimistic, with their mortality reaching 50% after 5 years of onset and 90% after 10 years of onset. It has been found that among the disease mechanisms which have been newly understood in the area of developing treatments for heart failure, cardiac remodeling, involving fibrosis that directly affects the cardiac pump function, and damage of cardiomyocytes interact with each other so that they are intimately linked to affect development, progression, and prognosis of diseases, and form a vicious cycle.

Therefore, since treatment of a single drug target or disease mechanism may cause insufficient results in treatment of heart failure, there is a need for studies on a new complex treatment to achieve functional recovery at the cellular level and to treat cardiac histological remodeling.

DISCLOSURE OF INVENTION

Technical Problem

The present inventors have studied to develop an effective treatment for heart failure, and as a result, have identified that a gene construct, an expression vector, and a recombinant virus, each of which comprises a nucleotide sequence encoding a SERCA2a protein or a fragment thereof and a nucleotide sequence encoding a CCN5 protein or a fragment thereof, exhibit a synergistic therapeutic effect on dysfunction caused by heart failure in a mouse model, in which the heart failure has been induced by multiple etiologies, thereby completing the present invention.

Solution to Problem

In an aspect of the present invention, there is provided a gene construct, comprising (i) a nucleotide sequence encoding a SERCA2a protein or a fragment thereof; and (ii) a nucleotide sequence encoding a CCN5 protein or a fragment thereof.

In another aspect of the present invention, there is provided a recombinant expression vector loaded with the gene construct.

In yet another aspect of the present invention, there is provided a recombinant virus comprising the gene construct.

In still yet another aspect of the present invention, there is provided a pharmaceutical composition for preventing or treating heart failure, comprising, as an active ingredient, the gene construct, the recombinant expression vector, or the recombinant virus.

In still yet another aspect of the present invention, there is provided a method for preventing or treating heart failure, comprising a step of administering the pharmaceutical composition to a subject.

In still yet another aspect of the present invention, there is provided a pharmaceutical composition for preventing or treating heart failure, comprising an expression vector loaded with a nucleotide sequence encoding a SERCA2a protein or a fragment thereof; and an expression vector loaded with a nucleotide sequence encoding a CCN5 protein or a fragment thereof.

In still yet another aspect of the present invention, there is provided a pharmaceutical composition for preventing or treating heart failure, comprising a recombinant virus that contains a nucleotide sequence encoding a SERCA2a protein or a fragment thereof; and a recombinant virus that contains a nucleotide sequence encoding a CCN5 protein or a fragment thereof.

In still yet another aspect of the present invention, there is provided a method for preventing or treating heart failure, comprising a step of administering, to a subject, (i) an expression vector loaded with a nucleotide sequence encoding a SERCA2a protein or a fragment thereof; and (ii) an expression vector loaded with a nucleotide sequence encoding a CCN5 protein or a fragment thereof.

In still yet another aspect of the present invention, there is provided a method for preventing or treating heart failure, comprising a step of administering, to a subject, (i) a recombinant virus that contains a nucleotide sequence encoding a SERCA2a protein or a fragment thereof; and (ii) a recombinant virus that contains a nucleotide sequence encoding a CCN5 protein or a fragment thereof.

Advantageous Effects of Invention

A common feature of heart failure is that cardiomyocytes disappear and fibrosis of heart tissue progresses, and this structural remodeling of the heart causes dysfunction in the cardiac pump. However, disappearance of cardiomyocytes and fibrosis of cardiac tissue may vary depending on the stage of disease progression, and may interact with each other to show a vicious cycle. Therefore, simultaneously treating disappearance of cardiomyocytes and fibrosis of cardiac tissue may be the most effective treatment.

The pharmaceutical composition for preventing and treating heart failure, of the present invention, is such that a SERCA2a protein and a CCN5 protein are simultaneously expressed. The pharmaceutical composition can exert a synergistic therapeutic effect through prevention of disappearance of cardiomyocytes and increased activity thereof achieved by the SERCA2a protein as well as prevention of fibrosis of cardiac cells and tissues achieved by the CCN5 protein, and thus can be effectively used for prevention or treatment of heart failure that is a complex disease induced by various etiologies.

BRIEF DESCRIPTION OF DRAWINGS

FIG. 1*a* illustrates a structure of pTR-CMV-SERCA2a vector.

FIG. 1*b* illustrates a structure of pTR-CMV-CCN5 vector.

FIG. 1*c* illustrates a structure of pTR-CMV-SERCA2a-P2A-CCN5 vector.

FIG. 1*d* illustrates a structure of pTR-CMV-CCN5-P2A-SERCA2a vector.

FIG. 2*a* illustrates results for intracellular expression and extracellular expression of pTR-CMV-SERCA2a, pTR-CMV-CCN5, and pTR-CMV-SERCA2a-P2A-CCN5.

FIG. 2*b* illustrates results comparing $Ca^{2+}$ reuptake activity of SERCA2a protein expressed in cells transformed with pTR-CMV-SERCA2a-P2A-CCN5 or pTR-CMV-CCN5-P2A-SERCA2a (n=5, **<0.01).

FIG. 2c illustrates results for expression levels of SERCA2a protein and CCN5 protein in cells transformed with pTR-CMV-SERCA2a-P2A-CCN5 or pTR-CMV-CCN5-P2A-SERCA2a.

FIG. 3 illustrates a conceptual diagram of animal experiments using mice in which heart failure has been induced by ischemia-reperfusion injury.

FIG. 4a illustrates results identifying expression of SERCA2a protein and CCN5 protein in cardiac tissues obtained by administering, to mice in which heart failure has been induced by ischemia-reperfusion injury, AAV9-Control, AAV9-SERCA2a, AAV9-CCN5, AAV9-SERCA2a+AAV9-CCN5 recombinant viruses.

FIG. 4b illustrates results comparing expression levels of SERCA2a protein in cardiac tissues (n=5, *<0.05, **<0.01) obtained by administering, to mice in which heart failure has been induced by ischemia-reperfusion injury, AAV9-Control, AAV9-SERCA2a, AAV9-CCN5, AAV9-SERCA2a+AAV9-CCN5 recombinant viruses.

FIG. 4c illustrates results comparing expression levels of CCN5 protein in cardiac tissues (n=5, **<0.01) obtained by administering, to mice in which heart failure has been induced by ischemia-reperfusion injury, AAV9-Control, AAV9-SERCA2a, AAV9-CCN5, AAV9-SERCA2a+AAV9-CCN5 recombinant viruses.

FIG. 5 illustrates photographs showing hearts extracted from mice obtained by administering, to the mice in which heart failure has been induced by ischemia-reperfusion injury, AAV9-Control, AAV9-SERCA2a, AAV9-CCN5, AAV9-SERCA2a+AAV9-CCN5 recombinant viruses: The area marked with a red line indicates an area where the heart tissue is infarcted.

FIG. 6 illustrates photographs showing hearts extracted from mice obtained by administering, to the mice in which heart failure has been induced by ischemia-reperfusion injury, AAV9-Control, AAV9-SERCA2a, AAV9-CCN5, AAV9-SERCA2a+AAV9-CCN5 recombinant viruses, and staining a cross section of heart tissue using the Picrosirius red method: The area marked with a red line indicates an area where the heart tissue is transmurally infarcted.

FIG. 7 illustrates results quantifying a proportion of infarct area in the extracted hearts (n=5, *<0.05, **<0.01) obtained by administering, to mice in which heart failure has been induced by ischemia-reperfusion injury, AAV9-Control, AAV9-SERCA2a, AAV9-CCN5, AAV9-SERCA2a+AAV9-CCN5 recombinant viruses.

FIG. 8 illustrates results showing fractional shortening (n=5, *<0.05, <0.01, *<0.001) obtained by administering, to mice in which heart failure has been induced by ischemia-reperfusion injury, AAV9-Control, AAV9-SERCA2a, AAV9-CCN5, AAV9-SERCA2a+AAV9-CCN5 recombinant viruses, and then performing echocardiography.

FIG. 9a illustrates results showing end-systolic pressure volume relationship (ESPVR) (n=5, *<0.05, <0.01, *<0.001) obtained by administering, to mice in which heart failure has been induced by ischemia-reperfusion injury, AAV9-Control, AAV9-SERCA2a, AAV9-CCN5, AAV9-SERCA2a+AAV9-CCN5 recombinant viruses, and then measuring hemodynamics.

FIG. 9b illustrates results showing end-diastolic pressure volume relationship (EDPVR) (n=5, *<0.05, **<0.01) obtained by administering, to mice in which heart failure has been induced by ischemia-reperfusion injury, AAV9-Control, AAV9-SERCA2a, AAV9-CCN5, AAV9-SERCA2a+AAV9-CCN5 recombinant viruses, and then measuring hemodynamics.

FIG. 10 illustrates a conceptual diagram of animal experiments using mice in which heart failure has been induced by transverse aortic constriction.

FIG. 11a illustrates results identifying expression of SERCA2a protein and CCN5 protein in cardiac tissues obtained by administering, to mice in which heart failure has been induced by transverse aortic constriction, AAV9-Control, AAV9-SERCA2a, AAV9-CCN5, AAV9-SERCA2a-P2A-CCN5 recombinant viruses.

FIG. 11b illustrates results comparing expression levels of SERCA2a protein in cardiac tissues (n=5, *<0.05, **<0.01) obtained by administering, to mice in which heart failure has been induced by transverse aortic constriction, AAV9-Control, AAV9-SERCA2a, AAV9-CCN5, AAV9-SERCA2a-P2A-CCN5 recombinant viruses.

FIG. 11c illustrates results comparing expression levels of CCN5 protein in cardiac tissues (n=5, **<0.01) obtained by administering, to mice in which heart failure has been induced by transverse aortic constriction, AAV9-Control, AAV9-SERCA2a, AAV9-CCN5, AAV9-SERCA2a-P2A-CCN5 recombinant viruses.

FIG. 12 illustrates photographs showing hearts extracted from mice obtained by administering, to the mice in which heart failure has been induced by transverse aortic constriction, AAV9-Control, AAV9-SERCA2a, AAV9-CCN5, AAV9-SERCA2a-P2A-CCN5 recombinant viruses, and staining a cross section of heart tissue using the Masson-trichrome staining method.

FIG. 13 illustrates results showing fractional shortening (n=5, *<0.05, **<0.01) obtained by administering, to mice in which heart failure has been induced by transverse aortic constriction, AAV9-Control, AAV9-SERCA2a, AAV9-CCN5, AAV9-SERCA2a-P2A-CCN5 recombinant viruses, and then performing echocardiography.

FIG. 14a illustrates results showing end-systolic pressure volume relationship (ESPVR) (n=5, *<0.05, **<0.01) obtained by administering, to mice in which heart failure has been induced by transverse aortic constriction, AAV9-Control, AAV9-SERCA2a, AAV9-CCN5, AAV9-SERCA2a-P2A-CCN5 recombinant viruses, and then measuring hemodynamics.

FIG. 14b illustrates results showing end-diastolic pressure volume relationship (EDPVR) (n=5, *<0.05, **<0.01) obtained by administering, to mice in which heart failure has been induced by transverse aortic constriction, AAV9-Control, AAV9-SERCA2a, AAV9-CCN5, AAV9-SERCA2a-P2A-CCN5 recombinant viruses, and then measuring hemodynamics.

FIG. 15 illustrates a conceptual diagram of animal experiments using mice in which heart failure has been induced by infusion of angiotensin II (AngII).

FIG. 16a illustrates results identifying expression of SERCA2a protein and CCN5 protein in cardiac tissues obtained by administering, to mice in which heart failure has been induced by infusion of angiotensin II, AAV9-Control, AAV9-SERCA2a, AAV9-CCN5, AAV9-SERCA2a-P2A-CCN5 recombinant viruses.

FIG. 16b illustrates results comparing expression levels of SERCA2a protein in cardiac tissues (n=5, **<0.01) obtained by administering, to mice in which heart failure has been induced by infusion of angiotensin II, AAV9-Control, AAV9-SERCA2a, AAV9-CCN5, AAV9-SERCA2a-P2A-CCN5 recombinant viruses.

FIG. 16c illustrates results comparing expression levels of CCN5 protein in cardiac tissues (n=5, *<0.05, **<0.01) obtained by administering, to mice in which heart failure has been induced by infusion of angiotensin II, AAV9-Control, AAV9-SERCA2a, AAV9-CCN5, AAV9-SERCA2a-P2A-CCN5 recombinant viruses.

FIG. 17 illustrates photographs showing hearts extracted from mice obtained by administering, to the mice in which heart failure has been induced by infusion of angiotensin II, AAV9-Control, AAV9-SERCA2a, AAV9-CCN5, AAV9-SERCA2a-P2A-CCN5 recombinant viruses, and staining a cross section of heart tissue using the Masson-trichrome staining method.

FIG. 18 illustrates results showing left ventricular wall thickness (n=5, *<0.05, **<0.01) obtained by administering, to mice in which heart failure has been induced by infusion of angiotensin II, AAV9-Control, AAV9-SERCA2a, AAV9-CCN5, AAV9-SERCA2a-P2A-CCN5 recombinant viruses, and then performing echocardiography.

FIG. 19 illustrates results showing fractional shortening (n=5, *<0.05, **<0.01) obtained by administering, to mice in which heart failure has been induced by infusion of angiotensin II, AAV9-Control, AAV9-SERCA2a, AAV9-CCN5, AAV9-SERCA2a-P2A-CCN5 recombinant viruses, and then performing echocardiography.

BEST MODE FOR CARRYING OUT THE INVENTION

In an aspect of the present invention, there is provided a gene construct comprising (i) a nucleotide sequence encoding SERCA2a protein or a fragment thereof; and (ii) a nucleotide sequence encoding CCN5 protein or a fragment thereof. Here, the nucleotide sequence may be in the form of mRNA.

As used herein, the term "SERCA2a protein," which is an abbreviation of sarcoplasmic reticulum calcium ATPase 2a, refers to a protein that functions to cause reuptake of calcium into the sarcoplasmic reticulum using ATP energy. Specifically, the SERCA2a protein may have the amino acid sequence represented by SEQ ID NO: 1. In addition, the nucleotide sequence encoding the SERCA2a protein may be the sequence represented by SEQ ID NO: 2 or SEQ ID NO: 13.

In addition, the fragment of the SERCA2a protein may be one obtained by truncation of a portion of the N-terminus and/or C-terminus of the wild-type SERCA2a as long as the fragment maintains activity of the SERCA2a protein. Specifically, the fragment of the SERCA2a protein may be one obtained by truncation of 1 to 100, 1 to 50, 1 to 20, or 1 to 10 amino acids from the N-terminus or C-terminus.

As used herein, the term "CCN5 protein" refers to a matricellular protein belonging to the CCN family that plays various roles in regulation of cellular functions such as vascular disease induction, angiogenesis, tumorigenesis, fibrosis disease induction, cell differentiation, and survival. The CCN5 protein, unlike other CCN family proteins, has no C-terminal domain and is also called WISP-2, HICP, Cop1, CTGF-L, or the like. In addition, the CCN5 protein consists of a single polypeptide chain having 250 amino acids. Owing to a 22-amino acid secretory leader sequence at the N-terminus, the CCN5 protein is secreted out of a cell and functions as a signaling protein.

Specifically, the CCN5 protein may have the amino acid sequence represented by SEQ ID NO: 3. In addition, the nucleotide sequence encoding the CCN5 protein may be the sequence represented by SEQ ID NO: 4 or SEQ ID NO: 14.

In addition, the fragment of the CCN5 protein may be one obtained by truncation of a portion of the N-terminus and/or C-terminus of the wild-type CCN5 as long as the fragment maintains activity of the CCN5 protein. Specifically, the fragment of the CCN5 protein may be one obtained by truncation of 1 to 30, 1 to 20, 1 to 10, or 1 to 5 amino acids from the N-terminus or C-terminus.

The gene construct may further comprise a self-cleavage sequence located between the nucleotide sequence (i) and the nucleotide sequence (ii). The self-cleavage sequence may be a 2A peptide sequence derived from positive-stranded RNA viruses such as Picornaviridae, Iflaviruses, Tetraviridae, and Discistroviridae, or a 2A peptide sequence derived from double-stranded RNA viruses such as Rotaviruses, Cypoviruses, and Totiviridae (Garry A Luke, et al Journal of General Virology, 2008; 89: 1036-1042).

A nucleotide sequence encoding a 2A peptide derived from porcine teschovirus-1, Thosea asigna virus, equine rhinitis A virus, or foot-and-mouth disease virus, which is typically widely used in research, may be present between the nucleotide encoding the SERCA2a protein or a fragment thereof and the nucleotide encoding the CCN5 protein or a fragment thereof. Specifically, the self-cleavage sequence may be, but is not limited to, a nucleotide sequence encoding a 2A peptide derived from porcine teschovirus-1. In addition, the self-cleavage sequence may be the nucleotide sequence represented by SEQ ID NO: 6.

The nucleotide sequence encoding the 2A peptide derived from porcine teschovirus-1 may be a nucleotide sequence encoding the amino acid sequence represented by SEQ ID NO: 5. In addition, the nucleotide sequence encoding the amino acid sequence represented by SEQ ID NO: 5 may be the nucleotide sequence represented by SEQ ID NO: 6.

The nucleotide sequence encoding the 2A peptide derived from Thosea asigna virus may be a nucleotide sequence encoding the amino acid sequence represented by SEQ ID NO: 7. In addition, the nucleotide sequence encoding the amino acid sequence represented by SEQ ID NO: 7 may be the nucleotide sequence represented by SEQ ID NO: 8.

The nucleotide sequence encoding the 2A peptide derived from equine rhinitis A virus may be a nucleotide sequence encoding the amino acid sequence represented by SEQ ID NO: 9. In addition, the nucleotide sequence encoding the amino acid sequence represented by SEQ ID NO: 9 may be the nucleotide sequence represented by SEQ ID NO: 10.

The nucleotide sequence encoding the 2A peptide derived from foot-and-mouth disease virus may be a nucleotide sequence encoding the amino acid sequence represented by SEQ ID NO: 11. In addition, the nucleotide sequence encoding the amino acid sequence represented by SEQ ID NO: 11 may be the nucleotide sequence represented by SEQ ID NO: 12.

Except for the 2A peptide sequence, which is a representative self-cleavage sequence, a variety of self-cleavage sequences exist, including Picornaviridae 2A sequences (for example, derived from Encephalomyocaditis virus, Theiler's murine encephalomyelitis virus, Theiler's-like virus, Saffold virus, equine rhinitis B virus, bovine rhinovirus, Ljungan virus, Seneca Valley virus, duck hepatitis virus) present in mammals, and 2A sequences derived from Iflaviruses (for example, infectious flacherie virus, Ectropisobliqua picorna-like virus, Perina nuda picorna-like virus), Tetraviruses (for example, Euprosterna elaeasa virus, Providence virus), or Dicistroviridae (for example, cricket paralysis virus, Drosophila C virus, Acute bee paralysis virus, Kashmir bee virus, Israeli acute bee paralysis virus) present in insects, among positive-stranded RNA viruses. In addition, among double-stranded RNA viruses, examples thereof may include Rotaviral 2A sequences (for example, derived from porcine rotavirus A, Bovine rotavirus C, Human rotavirus C, adult diarrhea virus) present in mammals, Cypoviral 2A sequences (for example, derived from Bombyx mori cytoplasmic polyhedrosis virus, Lymantria dispar cypovirus, Dendrolimus punctatus cypovirus, Operophtera brumata cypovirus) present in insects, and Totiviridae 2A sequences (for example, derived from infectious myonecrosis virus) present in Penaeid Shrimp. As such, various 2A sequences may exist, and these are not limited to the above.

In addition, in the gene construct, the nucleotide sequences (i) and (ii) may be contained, in 5' to 3' direction, in the order of (i)-(ii). When SERCA2a-P2A-CCN5, an embodiment of the gene construct, is expressed in a cell, the SERCA2a protein may be inserted into the sarcoplasmic reticulum membrane, and the CCN5 protein may be secreted out of the cell. In addition, when CCN5-P2A-SERCA2a, an embodiment of the gene construct of the present invention, is expressed in a cell, the SERCA2a protein may be inserted into the sarcoplasmic reticulum membrane, and the CCN5 protein may be secreted out of the cell.

In addition, the gene construct of (i) or (ii) may contain a promoter sequence operatively linked thereto.

As used herein, the term "operatively linked" refers to functional linkage between a nucleotide expression regulatory sequence (such as promoter, signal sequence, or array of transcription factor binding sites) and other nucleotide sequences. The regulatory sequence regulates transcription and/or translation of the other nucleotide sequences.

Specifically, a promoter linked to a nucleotide sequence encoding a SERCA2a protein or CCN5 protein may operate in animal cells, preferably in mammalian cells, to regulate transcription of the SERCA2a gene or the CCN5 gene. The promoter may include promoters derived from mammalian viruses and promoters derived from mammalian cell genomes. In addition, the promoter includes a synthetic promoter (synthetic muscle- and cardiac-restricted promoter, $SP_{C5-12}$) obtained by combination of genomic sequences of mammalian cells, intended to increase muscle- and heart-specific expression. The promoter may operate specifically in cardiac cells, and may also operate in any cells.

In an embodiment, the promoter may be linked in the form of i) promoter-SERCA2a-P2A-promoter-CCN5, ii) promoter-CCN5-P2A-SERCA2a, iii) promoter-SERCA2a-P2A-CCN5, or iv) promoter-CCN5-P2A-SERCA2a.

The promoter may be any one selected from the group consisting of cytomegalovirus (CMV) promoter, adenovirus late promoter, vaccinia virus 7.5K promoter, SV40 promoter, HSV tk promoter, RSV promoter, EF1 alpha promoter, metallothionein promoter, beta-actin promoter, human IL-2 gene promoter, human IFN gene promoter, human IL-4 gene promoter, human lymphotoxin gene promoter, and human GM-CSF gene promoter, as well as synthetic muscle- and cardiac-restricted promoter ($SP_{C5-12}$). However, the promoter is not limited thereto. Specifically, the promoter may be CMV promoter.

In addition, the gene construct of the present invention may be delivered into a cell using liposomes. Liposomes are formed automatically by phospholipids dispersed in the aqueous phase, and liposomes containing SERCA2a gene and CCN5 gene may interact with cells, through a mechanism such as endocytosis, adsorption to cell surface, or fusion with plasma cell membrane, thereby delivering the SERCA2a gene and the CCN5 gene into a cell.

In the present invention, when a pharmaceutical composition of the present invention is prepared based on a viral vector containing a gene construct, a method of administering the pharmaceutical composition may be performed according to virus infection methods known in the art. In addition, in the present invention, when the gene construct is contained in a naked recombinant DNA molecule or a plasmid, a microinjection method, a liposome-mediated transfection method, a DEAE-dextran treatment method, and a gene bombardment method may be used to introduce a gene into cells.

In another aspect of the present invention, there is provided a recombinant expression vector loaded with the gene construct.

As used herein, the term "expression vector" refers to a recombinant vector capable of expressing a target protein in a target host cell, the recombinant vector being a gene construct that contains essential regulatory elements operatively linked to a gene insert so that the gene insert is expressed.

In addition, the expression vector may contain a signal sequence in order for cells to facilitate protein secretion. Specific initiation signals may also be required for efficient translation of an inserted nucleic acid sequence. These signals contain the ATG start codon and contiguous sequences. Expression efficiency may be increased by introduction of an appropriate transcription- or translation-enhancing element.

The expression vector may be any one selected from the group consisting of plasmid vectors and cosmid vectors.

The plasmid vector may include, but is not limited to, commercially available plasmids such as pUC18, pBAD, and pIDTSAMRT-AMP.

In yet another aspect of the present invention, there is provided a recombinant virus, comprising the gene construct.

The virus may be any one selected from the group consisting of adenovirus, adeno-associated virus (AAV), retrovirus, lentivirus, herpes simplex virus, vaccinia virus, and the like. Specifically, the virus may be, but is not limited to, adeno-associated virus.

The adenovirus is widely used as a gene transfer vector because of its mid-sized genome, ease of manipulation, high titer, wide target-cell range, and excellent infectivity. Its genome may be flanked by 100 to 200 bp of inverted terminal repeat (ITR) which is an essential cis element for DNA replication and packaging. The adenovirus may further contain E1 regions (E1A and E1B) of the genome which encode proteins involved in viral DNA replication.

Among adenovirus vectors, replication-incompetent adenoviruses lacking the E1 regions may be used. On the other hand, E3 region is deleted from conventional adenovirus vectors to provide a site for insertion of a foreign gene.

Thus, a gene construct comprising the SERCA2a gene and the CCN5 gene, of the present invention, may be inserted into the deleted E1 regions (E1A region and/or E1B region, preferably E1B region) or E3 region. In an embodiment, the gene construct comprising the SERCA2a gene and the CCN5 gene may be inserted into the E3 region.

In addition, since up to approximately 105% of the wild-type genome can be packaged in adenovirus, about 2 kb may be additionally packaged in adenovirus. Thus, a foreign sequence to be inserted into adenovirus may be additionally linked to the adenoviral genome.

Adenovirus has 42 different serotypes and subgroups A to F. In an embodiment, the adenovirus vector of the present invention may be obtained from adenovirus type 5 belonging to subgroup C. Biochemical and genetic information on adenovirus type 5 is well known.

Foreign genes to be delivered by adenovirus replicate in the same way as episomes, and therefore, have very low genotoxicity to host cells.

The retrovirus is widely used as a gene transfer vector because the retrovirus is capable of inserting its gene into the host genome and delivering a large amount of foreign genetic material, and has a broad spectrum of cells it can infect. In order to construct a retroviral vector, the gene construct comprising the SERCA2a gene and the CCN5 gene may be inserted into the retroviral genome instead of the retroviral sequence to produce a replication-incompetent virus. In order to produce virions, a packaging cell line, which expresses gag, pol, and env genes, and does not express long terminal repeat (LTR) and $\Psi$ sequence, may be constructed and used.

The adeno-associated virus (AAV) is suitable as the gene delivery system of the present invention because it is capable of infecting non-dividing cells and has capacity to infect various types of cells. Details of construction and use of AAV vectors are disclosed in U.S. Pat. Nos. 5,139,941 and 4,797,368. Typically, AAV having a gene construct that contains SERCA2a gene and CCN5 gene may be produced by co-transformation of a plasmid containing the gene construct that contains SERCA2a gene and CCN5 gene, which is flanked by two AAV terminal repeats, and an expression plasmid containing the wild-type AVV coding sequence that lacks the terminal repeats.

Vectors derived from the vaccinia virus, the lentivirus, or the herpes simplex virus may also be used to deliver, into a cell, the CCN5 gene and the target nucleotide sequence to be delivered.

In still yet another aspect of the present invention, there is provided a pharmaceutical composition for preventing or treating heart failure, comprising, as an active ingredient, a gene construct, a recombinant expression vector, or a recombinant virus, of the present invention.

When a pharmaceutical composition of the present invention is made into preparations, examples of a pharmaceutically acceptable carrier to be contained therein may include, but are not limited to, lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil.

A dosage form of the pharmaceutical composition may vary depending on method of use, and may be made into injections.

A dose of the pharmaceutical composition of the present invention is desirably determined in consideration of the patient's age, sex, condition, degree of absorption of active ingredients in the body, inactivation rate, and drugs used in combination; and when the pharmaceutical composition is a virus, the pharmaceutical composition may be administered in an amount of $1.0 \times 10^3$ to $1.0 \times 10^{20}$ viral genomes per day on an adult basis. Specifically, the pharmaceutical composition of the present invention may be administered in an amount of $1.0 \times 10^3$ to $1.0 \times 10^{20}$, $1.0 \times 10^8$ to $1.0 \times 10^{16}$, $1.0 \times 10^{12}$ to $1.0 \times 10^{15}$, or $1.0 \times 10^{13}$ to $1.0 \times 10^{14}$ viral genomes per day on an adult basis.

In addition, when the pharmaceutical composition is a plasmid vector, the pharmaceutical composition may be administered at a concentration of 0.1 µg/1 µl to 1 mg/1 µl per day on an adult basis. In addition, when the pharmaceutical composition is a plasmid vector, the dose may include 0.1 ml, 1 ml, 2 ml, 3 ml, 4 ml, 5 ml, 6 ml, 7 ml, 8 ml, 9 ml, 10 ml or higher, and include all values and ranges therebetween.

In still yet another aspect of the present invention, there is provided a pharmaceutical composition for preventing or treating heart failure, comprising, as an active ingredient, SERCA2a protein and CCN5 protein.

A pharmaceutical composition of the present invention is parenterally administered, and the parental administration includes intravenous injection, subcutaneous injection, intramuscular injection, intraperitoneal injection, transdermal administration, method for direct injection into tissue, and the like.

As used herein, the term "acceptable carrier" refers to some or all of the following substances and includes those suitable for a particular dose: solvents, diluents, liquid vehicles, dispersants, suspension adjuvants, surfactants, isotonic agents, thickeners, emulsifiers, preservatives, solid binders, lubricants, or the like. Alfanso R. Gennaro, Remington's Pharmaceutical Sciences, 19$^{th}$ edition, 1995, Macna Publishing Co. Easton, PA presents various carriers for use in pharmaceutical compositions with known techniques and compositions. Examples of pharmaceutical composition of pharmaceutically acceptable carriers include, but are not limited to, the following. Glucose, sucrose sugar, starch such as corn starch and potato starch, cellulose and derivatives thereof such as sodium carboxymethyl cellulose, ethyl cellulose, and cellulose acetate; tragacanth in powder form; malt; gelatin; talc; excipients such as cocoa butter, suppository wax, peanut butter, cottonseed oil, safflower oil, sesame oil, olive oil, and soybean oil; glycols such as propylene glycol; esters such as ethyl oleate and ethyl laurate; agar; buffers such as magnesium hydroxide and aluminum hydroxide; alginic acid; pyrogen-free distilled water; isotonic saline; Ringer's solution; ethyl alcohol and phosphate buffered water, sodium lauryl sulfate and magnesium stearate, colorants, colorants, releasing agents, coating agents, sweeteners, flavoring agents and fragrances, antioxidants, and the like may be contained at the compound manufacturer's discretion.

In still yet another aspect of the present invention, there is provided a method for preventing or treating heart failure, comprising a step of administering the pharmaceutical composition to a subject.

Here, the subject may be a mammal, preferably a human. Specifically, the subject may be a human or a non-human mammal that is suffering from or may be at risk of heart failure.

In still yet another aspect of the present invention, there is provided a pharmaceutical composition for preventing or treating heart failure, comprising an expression vector loaded with a gene construct that contains a nucleotide sequence encoding a SERCA2a protein or a fragment thereof; and an expression vector loaded with a gene construct that contains a nucleotide sequence encoding a CCN5 protein or a fragment thereof.

The SERCA2a protein or a fragment thereof is as described above for the gene construct. The CCN5 protein or a fragment thereof is as described above for the gene construct.

In addition, the gene construct may contain a promoter sequence operatively linked thereto.

Specifically, a promoter linked to a nucleotide sequence encoding a CCN5 protein or a fragment thereof may operate, preferably in animal cells, and more preferably in mammalian cells, to regulate transcription of the CCN5 gene. The promoter includes promoters derived from the mammalian viruses and promoters derived from mammalian cell genomes. The promoter may operate specifically in cardiac cells, and may also operate in any cells.

The promoter is as described above, and may specifically be a CMV promoter.

In still yet another aspect of the present invention, there is provided a pharmaceutical composition for preventing or treating heart failure, comprising a recombinant virus containing a gene construct that contains a nucleotide sequence encoding a SERCA2a protein or a fragment thereof; and a recombinant virus containing a gene construct that contains a nucleotide sequence encoding a CCN5 protein or a fragment thereof.

The gene construct that contains the nucleotide sequence encoding the SERCA2a protein or a fragment thereof and the gene construct that contains the nucleotide sequence encoding the CCN5 protein or a fragment thereof are as described for the "pharmaceutical composition for preventing or treating heart failure, comprising an expression vector loaded with a gene construct that contains a nucleotide sequence encoding a SERCA2a protein or a fragment thereof; and an expression vector loaded with a gene construct that contains a nucleotide sequence encoding a CCN5 protein or a fragment thereof."

In still yet another aspect of the present invention, there is provided a method for preventing or treating heart failure, comprising the steps of (i) administering, to a subject, an expression vector loaded with a nucleotide sequence encoding a SERCA2a protein or a fragment thereof; and (ii) administering, to the subject, an expression vector loaded with a nucleotide sequence encoding a CCN5 protein or a fragment thereof.

Here, the subject may be a mammal, preferably a human. Specifically, the subject may be a human or another mammal that is suffering from or may be at risk of heart failure.

The administration steps (i) and (ii) may be carried out simultaneously. In addition, after the administration step (i) or (ii), the remaining administration step may be carried out at a time interval.

In still yet another aspect of the present invention, there is provided a method for preventing or treating heart failure, comprising the steps of (i) administering a recombinant virus that contains a nucleotide sequence encoding a SERCA2a protein; and (ii) administering a recombinant virus that contains a nucleotide sequence encoding a CCN5 protein.

Here, the subject may be a mammal, preferably a human. Specifically, the subject may be a human or another mammal that is suffering from or may be at risk of heart failure.

The administration steps (i) and (ii) may be carried out simultaneously. In addition, after the administration step (i) or (ii), the remaining administration step may be carried out at a time interval.

In still yet another aspect of the present invention, there is provided a use of a gene construct of the present invention for preventing or treating heart failure.

In still yet another aspect of the present invention, there is provided a use of a recombinant expression vector of the present invention for preventing or treating heart failure.

In still yet another aspect of the present invention, there is provided a use of a recombinant virus of the present invention for preventing or treating heart failure.

In still yet another aspect of the present invention, there is provided a use of a gene construct of the present invention for preparation of a pharmaceutical composition for preventing or treating heart failure.

In still yet another aspect of the present invention, there is provided a use of a recombinant expression vector of the present invention for preparation of a pharmaceutical composition for preventing or treating heart failure.

In still yet another aspect of the present invention, there is provided a use of a recombinant virus of the present invention for preparation of a pharmaceutical composition for preventing or treating heart failure.

MODE FOR THE INVENTION

Hereinafter, the present invention will be described in detail by way of experimental examples and examples. However, the following experimental examples and examples are only for illustrating the present invention, and the present invention is not limited to the following preparation examples and examples.

Preparation Example 1. Construction of Gene Constructs and AAV9-SRCA2a-P2A-CCN5

The gene constructs, PTR-CMV-SERCA2a, pTR-CMV-CCN5, pTR-CMV-SERC2a-P2A-CCN5, and pTR-CMV-CCN5-P2A-SERC2a, were constructed to express CCN5 protein and SERCA2a protein, either individually or simultaneously (FIGS. 1a to 1d).

The SERCA2a moiety consists of the entire cDNA sequence of human SERCA2a protein. The next linked P2A moiety is a self-cleavage site derived from porcine teschovirus-1 and consists of a nucleotide sequence encoding 22 amino acids. Lastly, the CCN5 moiety consists of the entire cDNA sequence of human CCN5 protein.

pTR-CMV-SERCA2a-P2A-CCN5 recombinant plasmid was completed by removing the luciferase moiety from pTR-CMV-luciferase vector and inserting the SERCA2a-P2A-CCN5 gene construct in place thereof. The protein produced by the recombinant plasmid is divided into the SERCA2a protein and the CCN5 protein by self-cleavage between the $21^{st}$ amino acid, glycine, and the $22^{nd}$ amino acid, proline, at the P2A site. The SERCA2a protein may remain in the endoplasmic reticulum membrane and perform its intrinsic function. In addition, the CCN5 protein may migrate into the endoplasmic reticulum and then be secreted out of the cell in the form in which the signal peptide is cleaved, thereby performing its intrinsic function. In contrast, pTR-CMV-CCN5-P2A-SERCA2a recombinant plasmid was also constructed by removing the luciferase moiety from pTR-CMV-luciferase vector and inserting the CCN5-P2A-SERCA2a gene construct in place thereof. Again, the protein produced thereby is divided into the SERCA2a protein and the CCN5 protein by the same function of the P2A sequence.

In order to produce self-complementary adeno-associated virus (AAV, serotype 9), human CCN5 gene and SERCA2a gene were cloned into pds-AAV2-EGFP vector. In order to improve virus packaging and viral delivery efficiency, eGFP sequence was removed during AAV vector construction. Recombinant AAV was constructed using 293T cells. AAV particles in a cell culture were collected and precipitated with ammonium sulfate. The resultant was purified by ultracentrifugation using iodixanol gradient. The AAV particles were enriched through several dilution and enrichment processes in such a manner that iodixanol is exchanged with lactated Ringer's solution using centrifugation. The AAV concentration was quantified using quantitative RT-PCR and SDS-PAGE.

Experimental Method 1. Calcium Uptake Assay

The 293T cell line having expressed the gene was homogenized in a solution, pH 7.0, containing 40 mM imidazole, 10 mM NaF, 1 mM EDTA, 300 mM sucrose, and 0.5 mM DTT, and 500 μg of lysate was added to an uptake reaction buffer, pH 7.0, of 100 mM KCl, 5 mM $MgCl_2$, 5 mM NaN3, 0.5 M EGTA, and 40 mM imidazole. Uptake experiments were performed using pCa 6 (0.0185 μmol) of calcium containing radioisotopes. Treatment with 1 μM Ruthenium red (Sigma Aldrich) was performed and the resultant was allowed to stand at temperature of 37° C. for 3 minutes. Then, reaction was allowed to start while performing treatment with 5 mM K-oxalate and Mg-ATP (Sigma Aldrich). 500 μl of the reaction product was filtered through a 0.45 μm filter (Millipore) up to 4 minutes at 1-minute intervals, and the count per minute (cpm) was measured using a scintillation counter (Beckman).

Experimental Method 2. Western Blotting

Cells or cardiac tissues were homogenized in a minimal volume of a 50 mM Tris-HCl solution, pH 7.4, to which a broad-spectrum protease inhibitor cocktail (Calbiochem) had been added. Proteins were separated by SDS-PAGE and transferred to polyvinylidene fluoride membrane (Schleicher & Schuell). After being blocked with 5% (w/v) skim milk for 1 hour and washed with TBST, the membrane was allowed to react with SERCA2a antibody ($21s^r$ Century Biochemical), CCN5 antibody (Sigma Aldrich), and GAPDH antibody (Sigma-Aldrich). The membrane was then reacted with horseradish peroxidase-conjugated secondary antibody (Jackson ImmunoResearch, WestGrove, PA, USA) and developed using a chemiluminescent substrate (Dogen). The resultant was photographed and quantified using LAS software.

Experimental Method 3. Tissue Staining

Cardiac tissues were taken from animal models and then fixed with 10% (w/v) formalin at room temperature for 5 days. Then, washing with PBS was performed. Each sample was embedded in paraffin and the tissue block was cut into 7 μm thick sections. In order to check degree of cardiac fibrosis and infarction, the resultant was stained with Picrosirius red (Sigma Aldrich) and Masson-Trichrome (Sigma Aldrich). Then, observations were made under an optical microscope.

Experimental Method 4. Measurement of Myocardial Function Through Echocardiography Mice were anesthetized by intraperitoneal injection of ketamine (95 mg/kg) and xylazine (5 mg/kg), and echocardiography was conducted. Recording was performed through 2-dimensional imaging and M-mode tracking function, and fractional shortening and ventricular size ratio were determined (GE Vivid Vision).

Experimental Method 5. Measurement of Myocardial Function Through Hemodynamics Measurement of hemodynamics in vivo was performed using a 1.2 Fr pressure-volume conductance catheter (Scisense Inc., Ontario, Canada). Mice were anesthetized by intraperitoneal injection of ketamine (95 mg/kg) and xylazine (5 mg/kg), intubated through tracheostomy, and ventilation was performed by adjusting mechanical air flow to 7 μl/g of tidal volume and 120 breaths per minute. A pressure-volume (PV) catheter was placed in the left ventricle and the pressure-volume data was analyzed using IOX2 software (emka TECHNOLOGIES).

Example 1. Identification of Protein Expression

In order to observe expression of the SERCA2a protein and the CCN5 protein by a recombinant plasmid of the present invention, pTR-CMV-SERA2a, pTR-CMV-CCN5, or pTR-CMV-SERCA2a-P2A-CCN5 prepared in Experimental Example 1 was delivered into cultured cells using lipofectamine. The obtained cells and cultures were subjected to Western blotting in the same manner as in Experimental Method 2, to check expression of SERCA2a, CCN5, and GAPDH proteins.

As a result, it was identified that in a case of being expressed by a single promoter, the SERCA2a protein is retained in the cytoplasm and the CCN5 protein is secreted out of the cell (FIG. 2a).

In addition, in order to compare protein expression level and activity of pTR-CMV-SERC2a-P2A-CCN5 and pTR-CMV-CCN5-P2A-SERC2a prepared in Experimental Example 1 were delivered into cultured cells using lipofectamine. The obtained cells and cultures were subjected to calcium uptake assay in the same manner as in Experimental Method 1.

As a result, no significant difference was observed in terms of expression level between the SERCA2a protein and the CCN5 protein, and the cells having expressed pTR-CMV-CCN5-P2A-SERC2a exhibited low calcium reuptake activity (FIGS. 2b and 2c).

This is due to the characteristic that the CCN5 protein is a secreted protein, suggesting that when the SERCA2a protein and the CCN5 protein are expressed in the order of SERCA2a-CCN5, both proteins are expressed in their normal structure, whereas when the SERCA2a protein and the CCN5 protein are expressed in the order of CCN5-SERCA2a, the SERCA2a protein, which is translated following the CCN5 protein, may be produced as an abnormal protein having topology that is opposite to its original topology.

I. Identification of Heart Failure Therapeutic Effect

In order to identify a heart failure therapeutic effect of a recombinant virus containing the gene construct that contains a nucleotide sequence encoding the SERCA2a protein and a nucleotide sequence encoding the CCN5 protein and, of the present invention, the mice, in which heart failure has been induced by multiple etiologies, were used.

For the heart failure-induced mice, an ischemia-reperfusion injury-induced heart failure model, a transverse aortic constriction-induced heart failure model, and an angiotensin II-induced heart failure model were produced. The heart failure-induced mice were divided into AAV9-Control, AAV9-SERCA2a administration group, AAV9-CCN5 administration group, and AAV9-SERCA2a-P2A-CCN5 administration group, and their heart failure therapeutic effects were compared.

Experimental Example 1. Identification of Heart Failure Therapeutic Effect in Mice in Which Heart Failure has been Induced by Ischemia-Reperfusion Injury

Experimental Example 1.1. Production of Mice, in which Heart Failure has been Induced by Ischemia-Reperfusion Injury, and Recombinant Virus Injection 8- to 10-week-old B6C3F1 mice were anesthetized by intraperitoneal injection of ketamine (95 mg/kg) and xylazine (5 mg/kg), and subjected to surgery. Ischemia was induced by placing polyethylene 10 (PE10) tubing with a diameter of 1 mm on top of the left anterior descending coronary artery and performing tying. After 30 minutes, reperfusion was induced by performing untying and removing the PE10 tubing. Simultaneously with inducing reperfusion, each mouse was injected, via the tail vein, with $1 \times 10^{11}$ viral genomes (vgs) of AAV9-Control, AAV9-CCN5, AAV9-SERCA2a, or AAV9-SERCA2a+AAV9-CCN5. After 4 weeks, myocardial function measurement and histological analysis were performed (FIG. 3).

Experimental Example 1.2. Identification of Expression of CCN5 Protein and/or SERCA2a Protein First, in order to identify whether effective delivery of the viral genome is made, expression of the SERCA2a protein and the CCN5 protein was checked through western blotting in the same manner as in Experimental Method 2.

As a result, it was identified that as compared with the AAV9-Control administration group, expression of the CCN5 protein was significantly increased in the AAV9-CCN5 administration group, and expression of the SERCA2a protein was significantly normalized in the AAV9-SERCA2a administration group. In addition, it was identified that in the AAV9-CCN5 and AAV9-SERCA2a combination administration group, expression of the CCN5 protein and the SERCA2a protein was significantly increased (FIGS. 4a to 4c).

Experimental Example 1.3. Identification of Heart Infarct Area-Decreasing Effect In addition, hearts were extracted from the mice, in which heart failure has been induced by ischemia-reperfusion injury, and photographed. Tissue staining was performed in the same manner as in Experimental Method 3.

As a result, the AAV9-CCN5 administration group, the AAV9-SERCA2a administration group, and the AAV9-CCN5 and AAV9-SERCA2a combination administration group exhibited a significantly decreased infarct area size, as compared with the infarct area in the AAV9-Control administration group. In particular, the AAV9-CCN5 and AAV9-SERCA2a combination administration group exhibited a remarkably decreased infarct area size (FIGS. 5 and 6). In addition, even from the graph obtained by quantifying a proportion of the infarct area out of the total heart area, it was identified that the AAV9-CCN5 and AAV9-SERCA2a combination administration group exhibited a remarkably decreased infarct area proportion (FIG. 7).

Experimental Example 1.4. Identification of Cardiac Contractility-Increasing Effect Echocardiography and hemodynamics were performed to identify whether morphological changes in heart tissue actually affect heart contractility.

In order to measure fractional shortening (FS), a parameter of cardiac contractility, echocardiography was performed in the same manner as in Experimental Method 4. As a result, it was identified that the fractional shortening, which has been decreased by ischemia-reperfusion injury, was significantly restored in the AAV9-CCN5 administration group, the AAV9-SERCA2a administration group, and the AAV9-CCN5 and AAV9-SERCA2a combination administration group. In particular, the AAV9-CCN5 and AAV9-SERCA2a combination group exhibited remarkably increased fractional shortening (FIG. 8).

In addition, hemodynamics measurement was conducted in the same manner as in Experimental Method 5, to accurately analyze cardiac contractility. As a result, the end-systolic pressure volume relationship (ESPVR), a parameter of systolic myocardial strength, was decreased by ischemia-reperfusion injury. The AAV9-SERCA2a administration group exhibited significantly increased ESPVR, and the AAV9-CCN5 administration group did not exhibit significantly increased ESPVR. This is the same phenomenon as known in the study of CCN5, supporting the fact that CCN5 does not affect heart failure. In addition, the AAV9-CCN5 and AAV9-SERCA2a combination group exhibited synergistically increased ESPVR (FIG. 9a).

In addition, it was identified that the end-diastolic pressure volume relationship (EDPVR), a parameter of diastolic myocardial strength, was increased upon ischemia-reperfusion injury. The AAV9-CCN5 administration group exhibited significantly decreased EDPVR, and the AAV9-SERCA2a administration group did not exhibit significantly decreased EDPVR. This is the same experimental result as previous studies, supporting the fact that the SERCA2a protein does not affect diastolic heart failure. In addition, the AAV9-CCN5 and AAV9-SERCA2a combination administration group exhibited remarkably decreased EDPVR (FIG. 9b).

Based on these data, it was identified that a synergistic therapeutic effect is obtained by combination administration of AAV9-CCN5 and AAV9-SERCA2a.

Experimental Example 2. Identification of Heart Failure Therapeutic Effect in Mice in which Heart Failure has been Induced by Transverse Aortic Constriction

Experimental Example 2.1. Production of Mice, in which Heart Failure has been Induced by Transverse Aortic Constriction, and Recombinant Virus Injection 8- to 10-week-old B6C3F1 mice were anesthetized by intraperitoneal injection of ketamine (95 mg/kg) and xylazine (5 mg/kg), and subjected to surgery. 2 to 3 mm of the proximal sternum was longitudinally dissected to ensure a visual field of the aortic arch. Thereafter, a 27-gauge needle was used to make a connection between the innominate artery and the carotid artery. Then, tying was performed and the needle was removed, thereby causing a constriction of transverse aorta. 8 Weeks after induction of heart failure with the constriction, each mouse was injected, via the tail vein, with $1 \times 10^{11}$ vgs of AAV9-Control, AAV9-CCN5, AAV9-SERCA2a, or AAV9-SERCA2a-P2A-CCN5. After 8 weeks, myocardial function measurement and histological analysis were performed (FIG. 10).

Experimental Example 2.2. Identification of Expression of CCN5 Protein and/or SERCA2a Protein First, in order to identify whether effective delivery of the viral genome was made, expression of the SERCA2a protein and the CCN5 protein was checked through western blotting in the same manner as in Experimental Method 2. As a result, it was identified that as compared with the AAV9-Control administration group, expression of the CCN5 protein was significantly increased in the AAV9-CCN5 administration group, and expression of the SERCA2a protein was significantly increased in the AAV9-SERCA2a administration group. In addition, it was identified that even in the AAV9-SERCA2a-P2A-CCN5 administration group, expression of the CCN5 protein and the SERCA2a protein was significantly increased (FIGS. 11a to 11c).

Experimental Example 2.3. Identification of Cardiac Internal Dimension Size-Decreasing Effect Hearts were extracted from the mice, in which heart failure had been induced by ischemia-reperfusion injury, and heart tissues were stained with Masson-trichrome in the same manner as in Experimental Method 3. As a result, it was identified that the AAV9-Control administration group exhibited an increased cardiac internal dimension size; and it was identified that the AAV9-CCN5 administration group, the AAV9-SERCA2a administration group, and the AAV9-SERCA2a-P2A-CCN5 administration group exhibited a decreased cardiac internal dimension size. In particular, it was identified that the AAV9-SERCA2a-P2A-CCN5 administration group exhibited a remarkably decreased internal dimension size. In addition, it was identified that the AAV9-CCN5 administration group, the AAV9-SERCA2a administration group, and the AAV9-SERCA2a-P2A-CCN5 administration group exhibited a decrease in degree of cardiac fibrosis caused by heart failure (FIG. 12).

Experimental Example 2.4. Identification of Heart Contractility-Increasing Effect Echocardiography and hemodynamics analysis were performed to identify whether morphological changes in heart tissue actually affect heart contractility.

In order to measure fractional shortening (FS), a parameter of cardiac contractility, echocardiography was performed in the same manner as in Experimental Method 4. As a result, it was identified that the fractional shortening, which has been decreased by aortic constriction, was significantly restored in the AAV9-CCN5 administration group, the AAV9-SERCA2a administration group, and the AAV9-CCN5 and AAV9-SERCA2a combination administration group. In particular, the AAV9-SERCA2a-P2A-CCN5 administration group exhibited remarkably increased fractional shortening (FIG. 13).

In addition, hemodynamics analysis was performed in the same manner as in Experimental Method 5, to accurately analyze cardiac contractility. As a result, the end-systolic pressure volume relationship (ESPVR), a parameter of systolic myocardial strength, was decreased by aortic constriction. The AAV9-SERCA2a administration group exhibited significantly restored ESPVR, and the AAV9-CCN5 administration group did not exhibit significantly restored ESPVR. In addition, the AAV9-SERCA2a-P2A-CCN5 administration group exhibited remarkably increased ESPVR (FIG. 14a).

In addition, it was identified that the end-diastolic pressure volume relationship (EDPVR), a parameter of diastolic myocardial strength, was increased upon ischemia-reperfusion injury. The AAV9-CCN5 administration group exhibited significantly decreased EDPVR, and the AAV9-SERCA2a administration group did not exhibit significantly decreased EDPVR. In addition, the AAV9-SERCA2a-P2A-CCN5 administration group exhibited remarkably decreased EDPVR (FIG. 14b). Based on this, it was identified that a synergistic therapeutic effect was obtained by AAV9-SERCA2a-P2A-CCN5.

Experimental Example 3. Identification of Heart Failure Therapeutic Effect in Mice in which Heart Failure has been Induced by Infusion of Angiotensin II (Ang II)

Experimental Example 3.1. Production of Mice, in which Heart Failure has been Induced by Infusion of Angiotensin II, and Recombinant Virus Injection 8- to 10-week-old B6C3F1 mice were anesthetized by intraperitoneal injection of ketamine (95 mg/kg) and xylazine (5 mg/kg), and heart failure was induced by subcutaneous infusion of angiotensin II (Ang II). Angiotensin II was infused subcutaneously for 2 weeks at a concentration of 3 mg/kg per day using a small osmotic pump (Alzet 1002, Alzet). 2 Weeks after induction of heart failure with Ang II, each mouse was injected, via the tail vein, with $1\times10^{11}$ viral genomes (vgs) of AAV9-Control, AAV9-CCN5, AAV9-SERCA2a, or AAV9-SERCA2a-P2A-CCN5. After 4 weeks, myocardial function measurement and histological analysis were performed (FIG. 15).

Experimental Example 3.2. Identification of Expression of CCN5 Protein and/or SERCA2a Protein First, in order to identify whether effective delivery of the viral genome is made, expression of the SERCA2a protein and the CCN5 protein was checked through western blotting in the same manner as in Experimental Method 2.

As a result, it was identified that as compared with the AAV9-Control administration group, expression of the CCN5 protein was significantly restored in the AAV9-CCN5 administration group, and expression of the SERCA2a protein was significantly restored in the AAV9-SERCA2a administration group. In addition, it was identified that even in the AAV9-SERCA2a-P2A-CCN5 administration group, expression of the CCN5 protein and the SERCA2a protein was significantly increased (FIGS. 16a to 16c).

Experimental Example 3.3. Identification of Cardiac Internal Dimension Size-Decreasing Effect and Changes in Inner Wall Thickness of Heart Hearts were extracted from the mice, in which heart failure had been induced by infusion of angiotensin II, and heart tissues were stained with Masson-trichrome in the same manner as in Experimental Method 3.

As a result, it was identified that the AAV9-Control administration group exhibited an increased cardiac internal dimension size; and it was identified that the AAV9-CCN5 administration group, the AAV9-SERCA2a administration group, and the AAV9-SERCA2a-P2A-CCN5 administration group exhibited a decreased cardiac internal dimension size. In particular, it was identified that the AAV9-SERCA2a-P2A-CCN5 administration group exhibited a remarkably decreased lumen size (FIG. 17).

In addition, echocardiography was performed in the same manner as in Example 6, to measure the inner wall thickness of the heart. Changes in the inner wall thickness of the heart were quantified and graphically represented.

As a result, it was identified that the inner wall thickness of the heart was decreased by infusion of angiotensin II, and it was identified that the AAV9-CCN5 administration group, the AAV9-SERCA2a administration group, and the AAV9-SERCA2a-P2A-CCN5 administration group exhibited a significantly restored increase in inner wall thickness of heart (FIG. 18).

Experimental Example 3.4. Identification of Heart Contractility-Increasing Effect Echocardiography and hemodynamics were performed to identify whether morphological changes in heart tissue actually affect heart contractility.

In order to measure fractional shortening (FS), a parameter of cardiac contractility, echocardiography was performed in the same manner as in Experimental Method 4. As a result, it was identified that the fractional shortening, which has been decreased by aortic constriction, was significantly restored in the AAV9-CCN5 administration group, the AAV9-SERCA2a administration group, and the AAV9-CCN5 and AAV9-SERCA2a combination administration group. In particular, the AAV9-SERCA2a-P2A-CCN5 administration group exhibited remarkably restored fractional shortening (FIG. 19). Based on this, it was identified that a synergistic therapeutic effect was obtained by AAV9-SERCA2a-P2A-CCN5.

The invention claimed is:

1. A gene construct comprising:
   (i) a nucleotide sequence encoding sarcoplasmic/endoplasmic reticulum Ca²+ATPase 2a (SERCA2a) protein; and
   (ii) a nucleotide sequence encoding cellular communication network factor 5 (CCN5) protein.

2. The gene construct of claim 1, wherein the SERCA2a protein has the amino acid sequence of SEQ ID NO: 1.

3. The gene construct of claim 2, wherein the nucleotide sequence encoding the SERCA2a protein is the sequence of SEQ ID NO: 2.

4. The gene construct of claim 1, wherein the CCN5 protein is has the amino acid sequence of SEQ ID NO: 3.

5. The gene construct of claim 4, wherein the nucleotide sequence encoding the CCN5 protein is the sequence of SEQ ID NO: 4.

6. The gene construct of claim 1, wherein the gene construct comprises a self-cleavage sequence located between the nucleotide sequences (i) and (ii).

7. The gene construct of claim 6, wherein the self-cleavage sequence is a nucleotide sequence encoding a 2A peptide obtained from porcine teschovirus-1, Thosea asigna virus, equine rhinitis A virus, or foot-and-mouth disease virus.

8. The gene construct of claim 6, wherein the self-cleaving sequence is a nucleotide sequence encoding 2A peptide obtained from porcine teschovirus-1.

9. The gene construct of claim 6, wherein the self-cleavage sequence is the nucleotide sequence of SEQ ID NO: 6.

10. The gene construct of claim 1, wherein the gene construct contains the nucleotide sequences (i) and (ii), in 5' to 3' direction, in the order of (i)-(ii).

11. The gene construct of claim 1, wherein the gene construct further contains a promoter sequence operatively linked thereto.

12. The gene construct of claim 11, wherein the promoter is any one selected from the group consisting of cytomegalovirus promoter, adenovirus late promoter, vaccinia virus 7.5K promoter, SV40 promoter, HSV tk promoter, RSV promoter, EF1 alpha promoter, metallothionein promoter, beta-actin promoter, human IL-2 gene promoter, human IFN gene promoter, human IL-4 gene promoter, human lymphotoxin gene promoter, human GM-CSF gene promoter, and synthetic muscle- and cardiac-restricted promoter.

13. A recombinant expression vector comprising the gene construct of claim 1.

14. The recombinant expression vector of claim 13, wherein the expression vector is any one selected from the group consisting of a plasmid vector and a cosmid vector.

15. A recombinant virus comprising the gene construct of claim 1.

16. The recombinant virus of claim 15, wherein the virus is any one selected from the group consisting of adenovirus, adeno-associated virus (AAV), retrovirus, lentivirus, herpes simplex virus and vaccinia virus.

17. The recombinant virus of claim 15, wherein the virus is adeno-associated virus.

18. A pharmaceutical composition comprising, as an active ingredient, the gene construct of claim 1, a recombinant expression vector comprising the gene construct, or a recombinant virus comprising the gene construct.

19. A method for treating heart failure, comprising a step of administering the pharmaceutical composition of claim 18 to a subject in need thereof.

20. A pharmaceutical composition comprising a first expression vector comprising a nucleotide sequence encoding a SERCA2a protein; and a second expression vector comprising a nucleotide sequence encoding a CCN5 protein.

21. A pharmaceutical composition comprising a first recombinant virus that contains a nucleotide sequence encoding a SERCA2a protein; and a second recombinant virus that contains a nucleotide sequence encoding a CCN5 protein.

22. A method for treating heart failure, comprising the steps of (i) administering, to a subject in need thereof, a first expression vector comprising a nucleotide sequence encoding a SERCA2a protein; and (ii) administering, to the subject, a second expression vector comprising a nucleotide sequence encoding a CCN5 protein.

23. The method of claim 22, wherein the administration steps (i) and (ii) are carried out simultaneously.

24. The method of claim 22, wherein, after the administration step (i) or (ii), the remaining administration step is carried out at a time interval.

25. A method for treating heart failure, comprising the steps of (i) administering a first recombinant virus that contains a nucleotide sequence encoding a SERCA2a protein; and (ii) administering a second recombinant virus that contains a nucleotide sequence encoding a CCN5 protein.

26. The method of claim 25, wherein the administration steps (i) and (ii) are carried out simultaneously.

27. The method of claim 25, after the administration step (i) or (ii), the remaining administration step is carried out at a time interval.

* * * * *